United States Patent
Ross

(10) Patent No.: US 10,773,065 B2
(45) Date of Patent: Sep. 15, 2020

(54) INCREASED BIOAVAILABILITY OF TRANSDERMALLY DELIVERED AGENTS

(71) Applicant: Sorrento Therapeutics, Inc., San Diego, CA (US)

(72) Inventor: Russell F. Ross, Atlanta, GA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 133 days.

(21) Appl. No.: 15/890,570

(22) Filed: Feb. 7, 2018

(65) Prior Publication Data

US 2018/0185626 A1    Jul. 5, 2018

Related U.S. Application Data

(63) Continuation of application No. 13/658,864, filed on Oct. 24, 2012, now abandoned.

(60) Provisional application No. 61/552,046, filed on Oct. 27, 2011.

(51) Int. Cl.
*A61M 37/00* (2006.01)
*A61K 9/00* (2006.01)

(52) U.S. Cl.
CPC ........ *A61M 37/0015* (2013.01); *A61K 9/0021* (2013.01); *A61M 2037/0023* (2013.01); *A61M 2037/0061* (2013.01)

(58) Field of Classification Search
CPC ...... A61M 37/0015; A61M 2037/0023; A61M 2037/003; A61M 2037/0046; A61M 2037/0061; A61M 2037/0038
See application file for complete search history.

(56) References Cited

U.S. PATENT DOCUMENTS

| | | | |
|---|---|---|---|
| 4,051,840 A | 10/1977 | Kantrowitz et al. |
| 4,698,062 A | 10/1987 | Gale et al. |
| 4,880,633 A | 11/1989 | Loper et al. |
| 6,132,755 A | 10/2000 | Eicher et al. |
| 6,334,856 B1 | 1/2002 | Allen et al. |
| 6,471,993 B1 | 10/2002 | Shastri et al. |

(Continued)

FOREIGN PATENT DOCUMENTS

| | | |
|---|---|---|
| EP | 2 100 850 A1 | 9/2009 |
| WO | WO 99/45860 A1 | 9/1999 |

(Continued)

OTHER PUBLICATIONS

Abstract of Japanese Patent—JPH08337521, Dec. 24, 1996, 2 pages.

(Continued)

*Primary Examiner* — Emily L Schmidt
(74) *Attorney, Agent, or Firm* — Armstrong Teasdale LLP

(57) ABSTRACT

A method for delivering a bioactive agent to the cardiovascular system is described. The method delivers the agent at a high bioavailability and with little loss of agent to the natural defense mechanisms of the body. For instance, little or none of the bioactive agent will be sequestered in lymph tissue and prevented from circulation in the cardiovascular system. The method includes utilization of a transdermal delivery device including microneedles with structures fabricated on a surface of the microneedles to form a nanotopography. A random or non-random pattern of structures may be fabricated such as a complex pattern including structures of differing sizes and/or shapes.

31 Claims, 18 Drawing Sheets

(56) References Cited

U.S. PATENT DOCUMENTS

| | | |
|---|---|---|
| 6,569,143 B2 | 5/2003 | Alchas et al. |
| 6,591,124 B2 | 7/2003 | Sherman et al. |
| 6,611,707 B1 | 8/2003 | Prausnitz et al. |
| 6,656,147 B1 | 12/2003 | Gertsek et al. |
| 6,663,820 B2 | 12/2003 | Arias et al. |
| 6,767,341 B2 | 7/2004 | Cho |
| 6,881,203 B2 | 4/2005 | Delmore et al. |
| 6,908,453 B2 | 6/2005 | Fleming et al. |
| 6,979,347 B1 | 12/2005 | Wu et al. |
| 6,980,855 B2 | 12/2005 | Cho |
| 6,995,336 B2 | 2/2006 | Hunt et al. |
| 7,048,723 B1 | 5/2006 | Frazier et al. |
| 7,066,922 B2 | 6/2006 | Angel et al. |
| 7,108,681 B2 | 9/2006 | Gartstein et al. |
| 7,115,108 B2 | 10/2006 | Wilkinson et al. |
| 7,129,554 B2 | 10/2006 | Lieber et al. |
| 7,131,987 B2 | 11/2006 | Sherman et al. |
| 7,185,663 B2 | 3/2007 | Koch et al. |
| 7,226,439 B2 | 6/2007 | Prausnitz et al. |
| 7,285,113 B2 | 10/2007 | Yeshurun |
| 7,315,758 B2 | 1/2008 | Kwiatkowski et al. |
| 7,332,339 B2 | 2/2008 | Canham |
| 7,364,568 B2 | 4/2008 | Angel et al. |
| 7,374,864 B2 | 5/2008 | Gua et al. |
| 7,410,476 B2 | 8/2008 | Wilkinson et al. |
| 7,416,541 B2 | 8/2008 | Yuzhakov et al. |
| 7,429,258 B2 | 9/2008 | Angel et al. |
| 7,473,244 B2 | 1/2009 | Frazier et al. |
| 7,531,120 B2 | 5/2009 | Van Rijn et al. ............... 9/1 |
| 7,537,590 B2 | 5/2009 | Santini, Jr. et al. |
| 7,556,615 B2 | 7/2009 | Pettis et al. |
| 7,572,405 B2 | 8/2009 | Sherman et al. |
| 7,578,954 B2 | 8/2009 | Gartstein |
| 7,582,069 B2 | 9/2009 | Laurent et al. |
| 7,588,552 B2 | 9/2009 | Yeshunan |
| 7,611,481 B2 | 11/2009 | Cleary et al. |
| 7,627,938 B2 | 12/2009 | Kim et al. |
| 7,658,728 B2 | 2/2010 | Yuzhakov |
| 7,753,888 B2 | 7/2010 | Mukerjee et al. |
| 7,785,301 B2 | 8/2010 | Yuzhakov |
| 7,803,574 B2 | 9/2010 | Desai et al. |
| 7,828,827 B2 | 11/2010 | Gartstein et al. |
| 7,846,488 B2 | 12/2010 | Johnson et al. |
| 7,855,046 B2 | 12/2010 | Suleski |
| 7,901,387 B2 | 3/2011 | Stemme et al. |
| 7,914,480 B2 | 3/2011 | Cleary et al. |
| 7,914,813 B2 | 3/2011 | Adachi et al. |
| 7,918,814 B2 | 4/2011 | Prausnitz et al. |
| 7,972,616 B2 | 7/2011 | Dubrow et al. |
| 7,981,346 B2 | 7/2011 | Griss et al. |
| 7,997,274 B2 | 8/2011 | Baska |
| 8,052,633 B2 | 11/2011 | Kendall |
| 8,057,842 B2 | 11/2011 | Choi et al. |
| 8,088,321 B2 | 1/2012 | Ferguson et al. |
| 8,097,456 B2 | 1/2012 | Borenstein et al. |
| 8,118,753 B2 | 2/2012 | Cho et al. |
| 8,137,736 B2 | 3/2012 | Zhu et al. |
| 8,162,901 B2 | 4/2012 | Gonnelli et al. |
| 8,238,995 B2 | 8/2012 | Chandrasekaran et al. |
| 8,366,677 B2 | 2/2013 | Kaspar et al. |
| 8,389,205 B2 | 3/2013 | Duerig et al. |
| 8,419,708 B2 | 4/2013 | Tokumoto et al. |
| 8,506,530 B2 | 8/2013 | Laermer et al. |
| 8,574,615 B2 | 11/2013 | Tenney et al. |
| 8,690,838 B2 | 4/2014 | Ozawa et al. |
| 8,696,637 B2 | 4/2014 | Ross |
| 8,915,957 B2 | 12/2014 | Arney et al. |
| 8,944,804 B2 | 2/2015 | Robeson et al. |
| 9,028,409 B2 | 5/2015 | Yodfat et al. |
| 2002/0082543 A1 | 6/2002 | Park et al. |
| 2002/0133129 A1 | 9/2002 | Arias et al. |
| 2002/0183688 A1 | 12/2002 | Lastovich et al. |
| 2003/0045837 A1* | 3/2003 | Delmore .......... A61M 37/0015 |
| | | 604/173 |
| 2004/0028875 A1 | 2/2004 | Van Rijn et al. |
| 2004/0063100 A1 | 4/2004 | Wang |
| 2004/0087992 A1 | 5/2004 | Gartstein et al. |
| 2005/0049625 A1 | 3/2005 | Shaya et al. |
| 2005/0112135 A1 | 5/2005 | Cormier et al. |
| 2005/0118388 A1 | 6/2005 | Kingsford |
| 2005/0119723 A1 | 6/2005 | Peacock, III |
| 2005/0124967 A1 | 6/2005 | Kaestner et al. |
| 2005/0137531 A1 | 6/2005 | Prausnitz et al. |
| 2005/0178760 A1 | 8/2005 | Chang et al. |
| 2005/0203613 A1 | 9/2005 | Arney et al. |
| 2006/0024358 A1 | 2/2006 | Santini, Jr. et al. |
| 2006/0025848 A1 | 2/2006 | Weber et al. |
| 2006/0051404 A1 | 3/2006 | Yeshurun et al. |
| 2006/0204738 A1 | 9/2006 | Dubrow et al. |
| 2006/0264893 A1 | 11/2006 | Sage, Jr. et al. |
| 2007/0066934 A1 | 3/2007 | Etheredge, III et al. |
| 2007/0078376 A1 | 4/2007 | Smith |
| 2007/0081977 A1 | 4/2007 | Horstmann |
| 2007/0088248 A1* | 4/2007 | Glenn .................. A61B 17/205 |
| | | 604/46 |
| 2007/0110810 A1 | 5/2007 | Smith |
| 2007/0112309 A1 | 5/2007 | Zucker |
| 2007/0112548 A1 | 5/2007 | Dickerson et al. |
| 2007/0191761 A1 | 8/2007 | Boone et al. |
| 2007/0249552 A1 | 10/2007 | Khalili et al. |
| 2007/0250018 A1 | 10/2007 | Adachi et al. |
| 2007/0282247 A1* | 12/2007 | Desai ...................... A61L 29/16 |
| | | 604/19 |
| 2008/0091226 A1 | 4/2008 | Yeshurun et al. |
| 2008/0097352 A1 | 4/2008 | Beck et al. |
| 2008/0108958 A1 | 5/2008 | Carter et al. |
| 2008/0195035 A1 | 8/2008 | Frederickson et al. |
| 2008/0200883 A1 | 8/2008 | Tomono |
| 2008/0208076 A1 | 8/2008 | Cho et al. |
| 2008/0217180 A1 | 9/2008 | Doye et al. |
| 2008/0221408 A1 | 9/2008 | Hoarau et al. |
| 2008/0262416 A1 | 10/2008 | Duan et al. |
| 2008/0269666 A1 | 10/2008 | Wang et al. |
| 2008/0269685 A1 | 10/2008 | Singh et al. |
| 2008/0305989 A1 | 12/2008 | Wen et al. |
| 2008/0311172 A1 | 12/2008 | Schapira et al. |
| 2008/0312610 A1 | 12/2008 | Binks et al. |
| 2009/0012494 A1 | 1/2009 | Yeshurun et al. |
| 2009/0043279 A1 | 2/2009 | Kaspar et al. |
| 2009/0069788 A1 | 3/2009 | Yeshurun et al. |
| 2009/0093776 A1 | 4/2009 | Yue et al. |
| 2009/0093871 A1 | 4/2009 | Rea et al. |
| 2009/0093879 A1 | 4/2009 | Wawro et al. |
| 2009/0099427 A1 | 4/2009 | Jina et al. |
| 2009/0099502 A1 | 4/2009 | Tokumoto et al. |
| 2009/0099537 A1 | 4/2009 | DeVoe et al. |
| 2009/0118662 A1 | 5/2009 | Schnall |
| 2009/0137926 A1 | 5/2009 | Srinivasan et al. |
| 2009/0177273 A1 | 7/2009 | Piveteau et al. |
| 2009/0198189 A1 | 8/2009 | Simons et al. |
| 2009/0232870 A1 | 9/2009 | Srivastava et al. |
| 2010/0004733 A1 | 1/2010 | Atanasoska et al. |
| 2010/0021464 A1 | 1/2010 | Archambeau et al. |
| 2010/0076035 A1 | 3/2010 | Carter et al. |
| 2010/0121307 A1 | 5/2010 | Lockard et al. |
| 2010/0168506 A1 | 7/2010 | Moon et al. |
| 2010/0215580 A1 | 8/2010 | Hanes et al. |
| 2010/0256568 A1 | 10/2010 | Frederickson et al. |
| 2010/0274203 A1 | 10/2010 | Lee et al. |
| 2011/0021996 A1 | 1/2011 | Lee et al. |
| 2011/0046557 A1 | 2/2011 | Lee et al. |
| 2011/0059150 A1 | 3/2011 | Kendall et al. |
| 2011/0144591 A1 | 6/2011 | Ross et al. |
| 2011/0270221 A1 | 11/2011 | Ross |
| 2011/0276003 A1 | 11/2011 | Luttge et al. |
| 2012/0089117 A1 | 4/2012 | Junginger et al. |
| 2012/0109065 A1 | 5/2012 | Backes |
| 2012/0128932 A1 | 5/2012 | Veith et al. |
| 2013/0144217 A1 | 6/2013 | Ross |
| 2013/0144257 A1 | 6/2013 | Ross |
| 2013/0165861 A1 | 6/2013 | Ross |
| 2013/0211310 A1 | 8/2013 | Bommarito et al. |

(56) References Cited

U.S. PATENT DOCUMENTS

| | | |
|---|---|---|
| 2013/0331792 A1 | 12/2013 | Karp et al. |
| 2014/0287019 A1 | 9/2014 | Ollerenshaw et al. |
| 2014/0343532 A1 | 11/2014 | Ross |

FOREIGN PATENT DOCUMENTS

| | | |
|---|---|---|
| WO | WO 00/74764 A1 | 12/2000 |
| WO | WO 01/75164 A2 | 10/2001 |
| WO | WO 02/30506 A2 | 4/2002 |
| WO | WO 02/32480 A2 | 4/2002 |
| WO | WO 02/091922 A1 | 11/2002 |
| WO | WO 03/020359 A2 | 3/2003 |
| WO | WO 03/024508 A2 | 3/2003 |
| WO | WO 03/059431 A1 | 7/2003 |
| WO | WO 03/092785 A1 | 11/2003 |
| WO | WO 2005/049128 A1 | 6/2005 |
| WO | WO 2006/062974 A2 | 6/2006 |
| WO | WO 2006/075689 A1 | 7/2006 |
| WO | WO 2007/012114 A1 | 2/2007 |
| WO | WO 2007/070004 A2 | 6/2007 |
| WO | WO 2007/081876 A2 | 7/2007 |
| WO | WO 2007/081876 A3 | 7/2007 |
| WO | WO 2007/112309 A2 | 10/2007 |
| WO | WO 2008/003564 A1 | 1/2008 |
| WO | WO 2008/024141 A2 | 2/2008 |
| WO | WO 2008/115883 A1 | 9/2008 |
| WO | WO 2009/079589 A2 | 6/2009 |
| WO | WO 2009/113856 A1 | 9/2009 |
| WO | WO 2010/062919 A1 | 6/2010 |
| WO | WO 2010/070628 A1 | 6/2010 |
| WO | WO 2010/087971 A2 | 8/2010 |
| WO | WO 2010/126640 A2 | 11/2010 |
| WO | WO 2011/116388 A1 | 9/2011 |
| WO | WO 2011/135531 A2 | 11/2011 |
| WO | WO 2012/046149 A1 | 4/2012 |

OTHER PUBLICATIONS

Abstract of Japanese Patent—JP2001238964. Sep. 4, 2001, 1 page.
Abstract of Japanese Patent—JP2008511382, Apr. 17, 2008,2 pages.
Abstract of Japanese Patent—JP2008237673, Oct. 9, 2008, 1 page.
Abstract of Japanese Patent—JP2009207733, Sep. 17, 2009, 1 page.
Ainslie et al., "Microfabricated Devices for Enhanced Bioadhesive Drug Delivery: Attachment to and Small-Molecule Release Through a Cell Monolayer Under Flow." Small. (2009).
Ainslie et al., "Microfabricated implants for applications in therapeutic delivery, tissue engineering, and biosensing." Royal Society of Chemistry. 8. (2008): 1864-1878.
Al-Qallaf et al., "Optimizing Microneedle Arrays to Increase Skin Permeability for Transdermal Drug Delivery," Interdisciplinary Transport Phenomena V: Ann. N.Y. Acad. Sci., 2009. pp. 1-12.
Bekarde, Iil Gercek. "Biomimetic Apatite-coated PCL Scaffolds: Effect of Surface Nanotopography on Cellular Functions." Journal of Bioactive and Compatible Polymers . 24.6 (2009): 507-524.
Berliner et al., "Impact of Transdermal Fentanyl on Quality of Life in Rheumatoid Arthritis", Clinical Journal of Pain, 2007, 23(6): 530-534.
Berry et al., "The interaction of human bone marrow cells with nanotopographical features in three dimensional constructs." Journal of Biomedical Materials Research Part A. 79A.2 (2006): 431-439.
Biehl et al., "Proliferation of Mouse Embryonic Stem Cell Progeny and the Spontaneous Contractile Activity of Cardiomyocytes Are Affected by Microtopography." Developmental Dynamics . 238. (2009): 1964-1973.
Biggs et al., "Interactions with nanoscale topsgraphy: Adhesion quantification and signal transduction in cells of osteogenic and multipotent lineage," *Journal of Biomedical Materials Research Part A*, 2008 Wiley Periodicals, Inc., pp. 195-208.
Chandler, David L.. "PhysOrg.com." Harnessing nanopatterns: Tiny textures can produce big differences. N.p., Sep. 24, 2009. Web. Dec. 1, 2009. <http://www.physorg.com/news173004362.html>.

Choi et al. "Cell interaction with three-dimensional sharp-tip nanotopography." Biomaterials. 28.9 (2007): 1672-1679.
Chun et al., "The role of polymer nanosurcace roughness and the submicron pores in improving bladder urothelial cell density and inhibiting calcium oxalate stone formation." Nanotechnology. 20.8 (2009): 85104.
Cohn, Abby. "Drug Delivery, Nanoscale." Innovations. 3.4 (2009).
Curtis et al., "Cell signaling arising from nanotopography: implicatinos for nanomedicaldevices." Nanomedicine. 1.1 (2006): 67-72.
Dalby et al, "Attempted endocytosis of nano-environment produced by colloidal lithography by human fibroblasts." Experimental Cell Research. 295. (2004): 387-394.
Dalby et al., "Increasing Fibroblast Response to Materials Using Nanotopography: Morphological and Genetic measurements of Cell Response to 13-nm-High Polymer Demixed Islands." Experimental Cell Research. 276.1 (2002): 1-9.
Dalby et al., "Nano-Topography Induces Mechanotransduction in Human Fibroblasts." European Cells and Materials . 6.2 (2003):31.
Dalby, Matthew J. "Nanostructured surfaces: cell engineering and cell biology." Nanomedicine. 4.3. (2009): 247-248.
Fischer et al., "Biomimetic Nanowire Coatings for Next Generation Adhesive Drug Delivery Systems." Nano Letters. 9.2 (2009): 716-720.
Hart et al., "Filapodial Sensing of Nanotopography in Osteoprogenitor Cells." European Cells and Materials . 10.2 (2005):65.
He, et al., "The anatase phase of nanotopography titania plays an important role on osteoblast cell morphology and proliferation", Journal of Mater. Sci: Mater Med (2008), 19:3465-3472.
Hu et al., "Surface Energy Induced Patterning of Polymer Nanostructures for Cancer Diagnosis and Therapy." IEEE Nano 2007 Conference Paper. (2007).
Kaushal et al, Influence of Piperline on Transcutaneous Permeation of Repaglinide in Rats and on Tight Junction Proteins in HaCaT Cells: Unveiling the Mechanisms for Enhanced Permeation; Sci. Pharm. 2009; 77; 877-897.
Kumar et al. "Transdermal Drug Delivery System: An Overview." International Journal of Pharmaceutical Sciences Review and Research. 3.2 (2010): 49-54.
Langeler et al., "Norepinephrine and iloprost improve barrier function of human endothelial cellmonolayers: role of cAMP", Am J Pli.ysio Cell Physiol, 1991, vol. 260(5), C1052-C1059.
Lim et al., "Human foetal osteoblastic cell response to polymer-demixed nanotopographic interfaces." Journal of the Royal Society Interface. 2.2 (2005): 97-108.
Madara, Jl, "Regulation of the movement of solutes across tight junctions", Annu Rev Physiol, 1998, 60:143-59.
Martinez-Palomo et al., "Experimental Modulation of Occluding Junctions in a Cultured Transporting Epithelium ", J. Cell Biology, 1980, 87; 736-745.
Meirelles et al., "The effect of chemical and nanotopographical modifications on the early stages of osseointegration." International Journal of Oral and Maxillofacial Implants. 23.4 (2008): 641-647.
Mendelsohn et al., "Inorganic Nanoporous Membranes for Immunoisolated Cell-Based Drug Delivery." Therapeutic Applications of Cell Microencapsulation. Dec. 15 , 2009.
Ng et al., "Study of substrate topographical affects on epithelial cell behavior using etched alpha-- particle tracks on PADC films." Nuclear Instruments and Methods in Physics Research Section B: Beam Interactions with Materials and Atoms. 266.14 (2008): 3247-3256.
Ojakian, Gk, "Tumor promotor-induced changes in the permeability of epithelial cell tight junctions", Cell. 1981, 23(1); 95-103.
Orr et al., "Submicrometer and Nanoscale Inorganic Particles Exploit the Actin Machinery to Be Propelled along Microvilli-likestructures into Alveolar Cells." American Chemical Society NANO. 1.5 (2007): 463-475.
Park et al., "Towards the silicon nanowire-based sensor for intracellular biochemical detection," *Biosensors and Bioelectronics*, vol. 22, No. 9-10, Apr. 1, 2007, 6 pages.
Sapra et al., "Effect of Asparagus racemous Extract on Transdermal Delivery of Carvedilol: A Mechanistic Study." American Association of Pharmaceutical Scientists PharmSciTech. 10.1 (2009): 199.

(56) References Cited

OTHER PUBLICATIONS

Sapra et al., "Transdermal Delivery of Carvedilol Containing Glycyrrhizin and Chitosan as Permeation Enhancers:Biochemical, Biophysical, Microscopic and Pharmacodynamic Evaluation." Drug Delivery . 15.7 (2008): 443-454.

Sapra et al., "Transdermal delivery of carvedilol in rats: probing the percutaneous permeation enhancement mechanism of soybean extract-chitosan mixture." Drug Delivery . 35.10 (2009): 1230-1241.

Thakar et al., "Contractility-Dependent Modulation of Cell Proliferation and Adhesion by Microscale Topographical Cues." Small. 4.9 (2008): 1416-1424.

Valenta et al., "The use of polymers for dermal and transdermal delivery." European Journal of Pharmaceutics and Biopharmaceutics. 58.2 (2004): 279-289.

Verma et al., "Development of Transdermal Drug Dosage Fomulation for the Anti-Rheumatic Ayurvedic Medicianal Plants", Ancient Sci. Life, 2007; 11:66-9.

Wang et al., "Nano patterned PDMS for periodontal ligament fibroblast culture," Surface and Coatings Technology.204.4 (2009): 525-530.

Wei et al., "Protein adsorption on materials surfaces with nano-topography." Chinese Science Bulletin. 52.23 (2007): 3169-3173.

Wood, M.A. "Colloidal lithography and current fabrication techniques producing in-plane nanotopography for biological applications," Journal of the Royal Society Interface. 4.12 (2007): 1-17.

Yao et al., "Nano-Surface Modification on Titanium Implants for Drug Delivery." Materials Research Society . (2007).

Yim et al., "Nanopattern-induced changes in morphology and motility of smooth muscle cells." Journal of Biomaterials. 58.1 (2005).

\* cited by examiner square packing hexagonal packing

DN1

Hole depth=500nm

DN2

Hole depth=500nm

DN3

Hole depth=500nm

DN4

Hole depth=400-500nm
(Random Variation)

NTTAT2

INCREASED BIOAVAILABILITY OF TRANSDERMALLY DELIVERED AGENTS

CROSS REFERENCE TO RELATED APPLICATIONS

This application is a continuation of U.S. application Ser. No. 13/658,1364 having a filing date of Oct. 24, 2012 which claims filing benefit of U.S. Provisional Patent Application Ser. No. 61/552,046 having a filing dated of Oct. 27, 2011, which are incorporated herein in their entirety.

BACKGROUND

Targeted drug delivery in which a bioactive agent (e.g., a drug or a therapeutic) is provided in an active state to a subject's system at effective concentrations is a long sought goal. Many difficulties must be overcome to reach this goal. For instance, an agent must first be successfully delivered internally, and the human body has developed many barriers to prevent the influx of foreign substances. Primary delivery methods presently used include oral delivery and injections. Both methods must overcome structural components that prevent delivery including the dermal barrier and the gastrointestinal lining. However, injections are painful, oral delivery often leads to gastrointestinal distress, and both methods tend to provide bursts of agents rather than a preferred steady-state delivery.

Transdermal delivery materials have been developed in an attempt to provide a painless route for successful delivery of active agents over a sustained period. In order to be successful, a transdermal scheme must deliver an agent across the epidermis, which has evolved with a primary function of keeping foreign substances out. The outermost layer of the epidermis, the stratum corneum, has structural stability provided by overlapping corneocytes and crosslinked keratin fibers held together by coreodesmosomes and embedded within a lipid matrix, all of which provides an excellent barrier function. Beneath the stratum corneum is the stratum granulosum, within which tight junctions are formed between keratinocytes. Tight junctions are barrier structures that include a network of transmembrane proteins embedded in adjacent plasma membranes (e.g., claudins, occludin, and junctional adhesion molecules) as well as multiple plaque proteins (e.g., ZO-1, ZO-2, ZO-3, cingulin, symplekin). Tight junctions are found in internal epithelium and endothelium (e.g., the intestinal epithelium, the blood-brain barrier) as well as in the stratum granulosum of the skin. Beneath both the stratum corneum and the stratum granulosum lays the stratum spinosum. The stratum spinosum includes Langerhans cells, which are dendritic cells that may become fully functioning antigen-presenting cells and may institute an immune response and/or a foreign body response to an invading agent.

Beyond the structural barriers to delivery of a bioactive agent, the body also has developed internal defense mechanisms, including the immune response and the foreign body response. Accordingly, even when a structural barrier has been breached, successful delivery of an agent requires avoidance of the internal defense mechanisms. When the body institutes an immune response and/or a foreign body response in an attempt to protect itself, the body's natural defenses will attempt to remove and/or destroy what is perceived as the invading agent. For successful systemic delivery, the bioactive agent must successfully enter the blood stream and pass through the lymph system, the liver, the spleen, etc. Identification of the bioactive agent as a foreign substance by the body's defenses will lead to at least partial removal of the agent from circulation, leading to lower levels of the agent remaining available for the desired use, i.e., lower bioavailability of the agent.

What are needed in the art are devices and methods that provide higher bioavailability of bioactive agents. More specifically, what are needed are devices and methods that can deliver a bioactive agent so as to successfully deliver the bioactive agent to the cardiovascular system and prevent targeting of the agent by the body's own defensive mechanisms.

SUMMARY

According to one embodiment, disclosed is a method for delivering a bioactive agent to a subject. The method includes penetrating the stratum corneum of the subject with a microneedle that is in fluid communication with the bioactive agent. In addition, the microneedle includes a plurality of nanostructures formed on a surface thereof in a pattern. The method also includes transporting the bioactive agent through the microneedle and delivering the bioactive agent to the subject with a comparative bioavailability as compared to a subcutaneous delivery route is greater than about 20%.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIG. 1 illustrates one embodiment of a microneedle device.

FIG. 2 illustrates another embodiment of a microneedle device.

FIG. 3 illustrates one embodiment of a microneedle including a surface that defines a nanotopography that may interact with an extracellular matrix (ECM).

FIG. 4 illustrates one embodiment of a complex pattern that may be formed on a microneedle surface.

FIG. 5 illustrates a pattern including multiple iterations of the complex pattern of FIG. 4.

FIG. 6 illustrates a Sierpinski triangle fractal.

FIG. 7A illustrates a complex nanotopography.

FIG. 7B illustrates another complex nanotopography.

FIG. 7C illustrates another complex nantopography.

FIG. 7D illustrates another complex nantopography.

FIG. 8 illustrates another complex pattern that may be formed on a microneedle surface.

FIG. 9A illustrates a square packing design as may be utilized for nano-sized structures as described herein.

FIG. 9B illustrates a hexagonal packing design as may be utilized for nano-sized structures as described herein.

FIG. 9C illustrates a circular packing design as may be utilized for nano-sized structures as described herein.

FIG. 10A schematically illustrates a first step in a nanoimprinting method as may be utilized in one embodiment in forming a device.

FIG. 10B schematically illustrates a second step in a nanoimprinting method as may be utilized in one embodiment in forming a device.

FIG. 10C schematically illustrates a third step in a nanoimprinting method as may be utilized in one embodiment in forming a device.

FIG. 11A illustrates an exploded view of a device as described herein.

Figure 29:
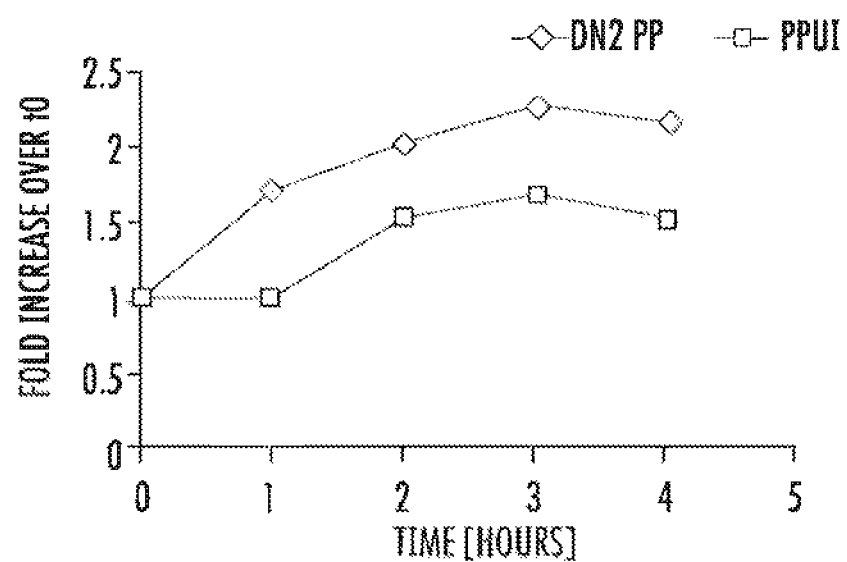

FIG. 29 graphically compares the delivery of a high molecular weight biological agent across a multilayer of cells on a film defining a nanopatterned surface as described herein and a multilayer of cells on a film with no nanostructures included on the surface.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

Methods are described herein that provide a route for delivering a bioactive agent, e.g., a drug or a therapeutic, across a dermal barrier of a subject with high bioavailability. More specifically, the methods can be used for transdermal delivery of a bioactive agent to the blood stream of a subject with little or none of the agent being removed from circulation by tissues associated with immune and foreign body response. For instance, following delivery of a bioactive agent across a dermal barrier, the bioactive agent can have a high bioavailability in the system. In addition, little or none of the agent can be detected in lymph tissue, the liver, the spleen or other organs associated with the body's natural defense mechanisms against an invading agent. Moreover, the bioactive agent can include high molecular weight bioactive agents, such as protein therapeutics having a molecular weight greater than about 100 kDa, which have proven very difficult in the past to deliver via transdermal delivery.

Subjects as may benefit from the methods can include any animal subject in need of delivery of a bioactive agent. For instance a subject can be a human or any other mammal or animal as may benefit from the delivery methods.

The delivery method utilizes a transdermal delivery device that includes one or more microneedles and a pattern of structures fabricated on a surface of at least one of the microneedles. In addition, at least a portion of the structures fabricated on a surface of the microneedle are fabricated on a nanometer scale. As utilized herein, the term 'fabricated' generally refers to a structure that has been specifically designed, engineered, and/or constructed so as to exist at a surface of a microneedle and is not to be equated with a surface feature that is merely an incidental product of the formation process. Thus, the transdermal delivery device will include a predetermined pattern of nanostructures on the surface of a microneedle.

Without wishing to be bound by any particular theory, it is believed that through interaction between the nanotopography on a surface of the microneedle and surrounding biological materials or structures, the microneedle as well as the bioactive agent delivered by the microneedle may avoid being targeted by the body's defense mechanisms. In addition, the fabricated pattern may regulate and/or modulate membrane potential, membrane proteins, and/or intercellular junctions (e.g., tight junctions, gap junctions, and/or desmasomes) of and between cells in the area surrounding the microneedle. More specifically, it is believed that interaction between the nanotopography of the microneedle and the surrounding biological materials can rearrange epithelial tight junctions of the dermal tissue and temporarily increase porosity of the local barrier structures. In addition, it is believed that this effect can not only occur at cells in contact with the microneedle, but this effect can be perturbed to other cells in the area, including cells of different tissue types. This can effectively translate the increased porosity effect to nearby structures and tissue types, which can increase porosity of nearby vasculature. This can encourage transport of the bioactive agent across not only the dermal barrier, but also across the vessel walls of the nearby vasculature and increase uptake of the bioactive agent by the cardiovascular system. Moreover, this transport can take place without triggering the defense mechanisms of the body, which can further increase bioavailability of the agent.

When a bioactive agent is delivered across the dermal barrier, it is delivered to connective tissue through which the vasculature passes. In order to reach the cardiovascular system the bioactive agent must either pass directly into the local vasculature, which requires passage through the vessel walls, or first pass into the lymph system. The lymphatic capillaries have thinner walls than do blood capillaries, have no basement membrane, and the endothelial cells merely overlap, with no tight binding between them. Thus, it is normally much easier for an agent, particularly a high molecular weight agent, to pass into the lymph system from the interstitial fluid as compared to the cardiovascular system. Once in the lymph system, an agent must successfully pass through the system, including the lymph nodes that include very high concentrations of lymphocytes, without being targeted as a pathogen. Upon successful passage through the lymph system, the agent will be dumped into the cardiovascular system, for instance at the thoracic duct or at the right lymphatic duct.

Through utilization of the nanostructured transdermal delivery devices, the permeability of barrier tissue in the localized area of the device is increased. Significantly, this increased permeability is understood to be not limited to either tissue in direct contact with the device or to the dermal layers. While not wishing to be bound to any particular theory, it is believed that the interaction between the device and the contacting tissue leads to the rearrangement of epithelial tight junctions of the dermal tissue, and this instigates a cascade response that transfers a similar effect to the walls of the local blood vessels, for instance both the basement membrane and the endothelium of a local capillary. This can lead to fenestration of the capillary wall, allowing entry of a bioactive agent directly to the cardiovascular system. Through by-passing the lymph system, the bioavailability of the bioactive agent can be greatly increased.

In addition to improving direct delivery of a bioactive agent to the cardiovascular system, the methods can also prevent recognition and targeting of a bioactive agent as an invading pathogen. When a foreign body crosses the dermal barrier and is recognized as such, extracellular matrix material or plasma proteins can aggregate to the foreign body. Depending upon the specific materials that aggregate to the foreign body, these materials can instigate various reactions including containment of the body and/or neutralization of the foreign body. For instance, when a delivery device, e.g., a microneedle of a device, is held in contact with a dermal barrier and is recognized as a foreign body, certain defense responses will ensue.

One of the initial responses upon recognition of a foreign body is increased blood flow to the local area resulting in inflammation. A consequence of inflammation is increased recruitment of immune cells and related extracellular materials to the local site. These materials can include proteins that can mark a body, e.g., a molecular body associated with the primary instigator of the response, as a foreign body. Accordingly, when a first body such as a microneedle is recognized as a foreign body, a cascade of initial responses ensues. Among these initial responses are those that can instigate a second response directed against the bioactive agent that is delivered by the device that has been recognized as a second foreign body.

Natural defense mechanisms directed to a bioactive agent delivered by a transdermal delivery device can include binding of proteins to the bioactive agent, thereby marking it as a foreign particle. When these marked particles travel through the body, for instance following entrance to the lymphatic vessels as a component of the interstitial fluid, they will be recognized as an antigen by lymphocytes, for instance during passage through the lymph nodes. Stimulation of the lymphocytes by the antigen can accelerate the migration of antibody-producing plasma cells to the medullary cord of the lymph node, which results in the characteristic swelling of the lymph nodes during infection. In addition, the recognition and marking of the bioactive agent can lead to accumulation of the bioactive agent in the lymph tissue as the marked agent is filtered and removed from circulation. When defense mechanisms are initiated due to the presence of a delivery device, a bioactive agent delivered by that device can be marked as a pathogen and can be removed from circulation and accumulate in lymph nodes as well as in organs that include a large amount of lymph tissue, e.g., a large amount of lymphoid follicles.

When bioactive agents marked as pathogen enter blood vessels rather than lymph vessels, they can initiate an immune response in the spleen or be marked for removal by hepatic clearance. Thus, the recognition of a delivery device as a foreign body can also lead to accumulation of bioactive agent in the spleen as well as in the liver, both of which contain a large number of immunologically active cells and filter and remove pathogens from the blood stream.

By use of the transdermal delivery method utilizing nanostructured microneedles, direct delivery of a bioactive agent to the cardiovascular system can be improved, particularly in the case of high molecular weight agents. In addition, the methods can prevent the targeting of the bioactive agent by the body's defense mechanisms as a pathogen. As a result, less of the bioactive agent will be lost through collection or destruction of the agent in the body's defense system and the bioavailability of the bioactive agent can be greatly increased.

In general, the term bioavailability refers to the fraction of an administered dose that reaches systemic circulation. A numerical value for the bioavailability can be the area under the pharmacokinetic curve, i.e., the integral of the curve defined by the change in serum concentration with respect to time, divided by the dose of the bioactive agent. For instance, the bioavailability can be characterized by the following relationship:

$$F = \frac{AUC}{\text{DOSE}} \times 100\%$$

Wherein AUC is the integral of the pharmacokinetic curve, and Dose is the dosage amount.

In one embodiment, the bioavailability can be reported as a comparative bioavailability ($F_{com}$), for instance the ratio of the bioavailability of an agent delivered according to the methods described herein compared to the bioavailability of the same agent delivered according to another method. When the second method is intravenous delivery, the comparative bioavailability is generally referred to as the absolute bioavailability, $F_{abs}$.

$$F_{abs} = \frac{AUC_{MN}}{AUC_{IV}} \times \frac{Dose_{IV}}{Dose_{MN}} \times 100\%$$

Wherein IV refers to the intravenous delivery method and MN refers to the second method, e.g., the microneedle delivery method.

In one embodiment, the comparative bioavailability can compare the bioavailability according to the methods described herein as compared to a subcutaneous delivery route, i.e.:

$$F_{com} = \frac{AUC_{MN}}{AUC_{SubQ}} \times \frac{Dose_{SubQ}}{Dose_{MN}} \times 100\%$$

Wherein MN is the nanostructured microneedle method and SubQ is the subcutaneous method.

By utilization of the transdermal delivery method described herein, the comparative bioavailability as compared to a subcutaneous delivery route can be greater than about 20%, greater than about 30%, or greater than about 35%.

In conjunction with high bioavailability, the concentration of a bioactive agent lost from circulation, e.g., sequestered in an organ of the body, and particularly organs associated with defense mechanisms, can be quite low. By way of example, the concentration of a bioactive agent found in the lateral aortic lymph nodes can be less than about 50 nanograms per gram of tissue (ng/g), less than about 40 ng/g, less than about 20 ng/g, less than about 10 ng/g, less than about 1 ng/g, or less than about 0.6 ng/g following delivery of the agent, for instance about 72 hours following delivery.

The concentration of a bioactive agent found in the spleen following delivery of the agent can be less than about 5 ng/g, less than about 3 ng/g, or less than about 1 ng/g and the concentration of a bioactive agent found in the liver can be less than about 50 ng/g, less than about 40 ng/g, less than about 20 ng/g, less than about 10 ng/g, or less than about 1 ng/g.

Moreover, even in organs not directly associated with the body's natural defense mechanisms, due to the improved bioavailability of a bioactive agent and associated improved circulation of the agent within the cardiovascular system, the concentration of a bioactive agent within the organs can be low. For instance, the concentration of a bioactive agent within an organ following administration of the agent can be less than about 50 ng/g, less than about 25 ng/g, or less than about 15 ng/g. Organs for determination of concentration can include any organs of the body including, without limitation, the pancreas, the skin, the lung, the bones (e.g., the bone marrow, and the kidney.

Following application of the transdermal delivery device to the skin, generally in the form of a patch, a subject can exhibit a PK profile that reflects a rapid rise in blood serum concentration up to between about 500 and about 1000 nanograms of the bioactive agent per milliliter per square centimeter of patch area, for instance between about 750 and about 850 nanograms bioactive agent per milliliter per square centimeter patch area, within about 1 to about 4 hours of administration. This initial rapid rise in blood serum level, which reflects rapid uptake of the bioactive agent across the dermal barrier, can be followed by a less rapid decline of blood serum concentration over between about 20 and about 30 hours, for instance over about 24 hours, down to a negligible blood serum concentration of the bioactive agent.

There is no particular limitation to bioactive agents as may be delivered by use of the methods. Bioactive agents can encompass natural or synthetic agents, small molecule agents, and so forth. In one embodiment, methods may be utilized for delivery of high molecular weight bioactive agents (e.g., non-proteinaceous synthetic or natural bioactive agents defining a molecular weight greater than about 400 Da, greater than about 10 kDa, greater than about 20 kDa, or greater than about 100 kDa, e.g., about 150 kDa).

In one particular example, a bioactive agent delivered according to the methods can be a high molecular weight protein therapeutic. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. By way of example, a protein therapeutic having a molecular weight of greater than about 100 kDa, or greater than about 125 kDa, for instance from about 125 kDa to about 200 kDa, or from about 150 kDa to about 200 kDa, can be delivered transdermally via the methods.

Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs that regulate cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally Injecting Substances", the entire content of which is incorporated herein by reference. Vaccine formulations may include an antigen or antigenic composition capable of eliciting an immune response against a human pathogen or from other viral pathogens.

In one embodiment, methods may be utilized in treatment of a chronic condition, such as rheumatoid arthritis, to deliver a steady flow of an agent, to a subject in need thereof. RA drugs that can be delivered can include symptom suppression compounds, such as analgesics and anti-inflammatory drugs including both steroidal and non-steroidal anti-inflammatory drugs (NSAID), as well as disease-modifying antirheumatic drugs (DMARDs).

RA drugs can include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs can likewise function as a DMARD as well as an anti-inflammatory. Moreover, multiple compounds that can fall under a single category can be delivered. For instance, methods can be utilized to deliver multiple analgesics, such as acetaminophen with codeine, acetaminophen with hydrocodone (vicodin), and so forth.

A transdermal delivery device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon, silicon dioxide, and polymers may be utilized. Typically, the device is formed of a biocompatible material that is capable of carrying a pattern of structures as described herein on a surface. The term "biocompatible" generally refers to a material that does not substantially adversely affect the cells or tissues in the area where the device is to be delivered. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with polyethylene glycol, polyanhydrides, poly(ortho)esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluorethylene, and polyesters. The device may likewise be non-porous or porous in nature, may be homogeneous or heterogeneous across the device with regard to materials, geometry, solidity, and so forth, and may have a rigid fixed or a semi-fixed shape.

Figure 1:
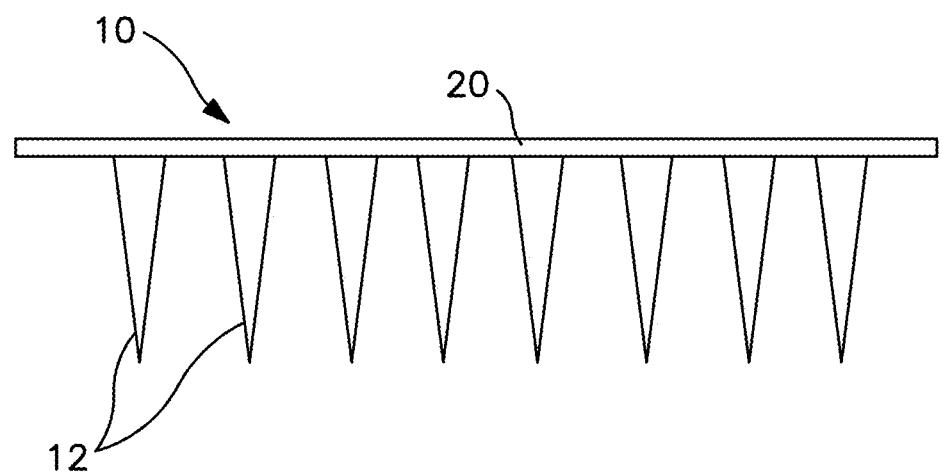
Figure 2:
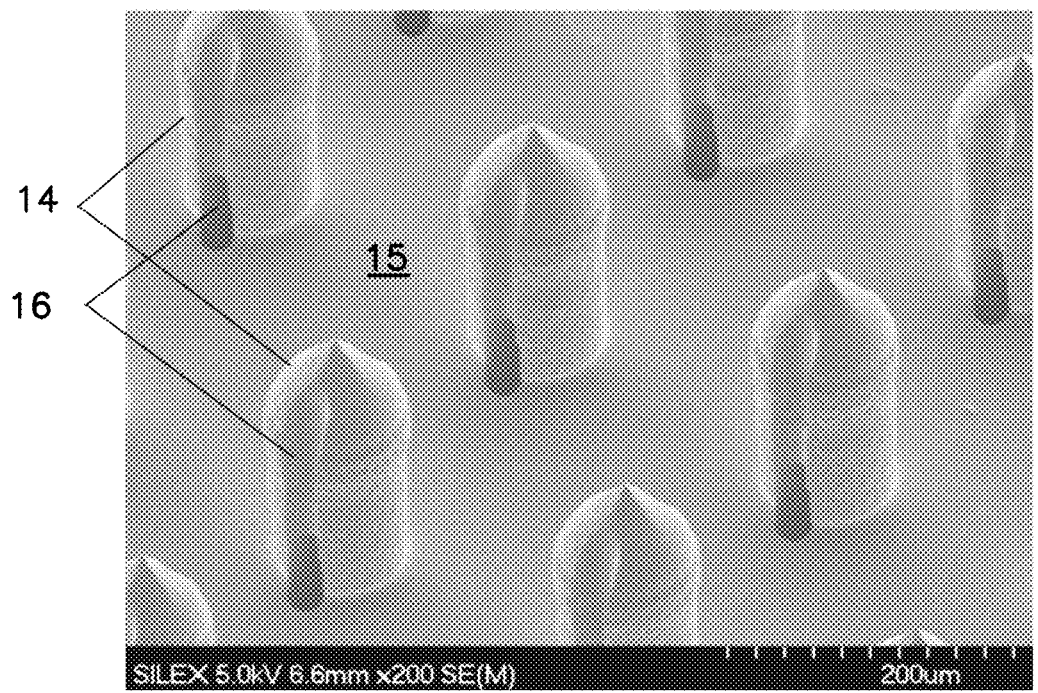

FIG. 1 illustrates a typical microneedle transdermal delivery device 10. As may be seen, the device includes an array of individual needles 12; each formed to a size and shape so as to penetrate a biological barrier without breakage of the individual microneedles. Microneedles may be solid, as in FIG. 1, porous, or may include a hollow portion. A microneedle may include a hollow portion, e.g., an annular bore that may extend throughout all or a portion of the needle, extending parallel to the direction of the needle or branching or exiting at a side of the needle, as appropriate. For example, FIG. 2 illustrates an array of microneedles 14 each including a channel 16 in a side of the needles as may be utilized for, e.g., delivery of an agent to a subdermal location. For instance, a channel 16 may be in at least partial alignment with an aperture in base 15 so as to form a junction between the aperture and channel 16 allowing the passage of a substance through the channel 16.

The dimensions of the channel 16, when present, can be specifically selected to induce capillary flow of a composition including a bioactive agent. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or length vary as a function of length, the aspect ratio can be determined from the average dimensions.

It should be understood that the number of microneedles shown in the figures is for illustrative purposes only. The actual number of microneedles used in a microneedle assembly may, for example, range from about 500 to about 10,000, in some embodiments from about 2,000 to about 8,000, and in some embodiments, from about 4,000 to about 6,000.

An individual microneedle may have a straight or a tapered shaft. In one embodiment, the diameter of a microneedle may be greatest at the base end of the microneedle and taper to a point at the end distal the base. A microneedle may also be fabricated to have a shaft that includes both a straight (untapered) portion and a tapered portion.

A microneedle may be formed with a shaft that is circular or non-circular in cross-section. For example, the cross-section of a microneedle may be polygonal (e.g., star-shaped, square, triangular), oblong, or any other shape. The shaft may have one or more bores and/or channels.

The size of individual needles may be optimized depending upon the desired targeting depth, the strength requirements of the needle to avoid breakage in a particular tissue type, etc. For instance, the cross-sectional dimension of a transdermal microneedle may be between about 10 nanometers (nm) and 1 millimeter (mm), or between about 1 micrometer (μm) and about 200 micrometers, or between about 10 micrometers and about 100 micrometers. The outer diameter may be between about 10 micrometers and about 100 micrometers and the inner diameter of a hollow needle may be between about 3 micrometers and about 80 micrometers. The tip typically has a radius that is less than or equal to about 1 micrometer.

The length of a microneedle will generally depend upon the desired application. For instance, a microneedle may be from about 1 micrometer to about 1 millimeter in length, for instance about 500 micrometers or less, or from about 10 micrometers to about 500 micrometers, or from about 30 micrometers to about 200 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

Referring again to FIG. 1, microneedles may be held on a substrate 20 (i.e., attached to or unitary with a substrate) such that they are oriented perpendicular or at an angle to the substrate. In one embodiment, the microneedles may be oriented perpendicular to the substrate and a larger density of microneedles per unit area of substrate may be provided. However, an array of microneedles may include a mixture of microneedle orientations, heights, materials, or other parameters. The substrate 20 may be constructed from a rigid or flexible sheet of metal, ceramic, plastic or other material. The substrate 20 can vary in thickness to meet the needs of the device, such as about 1000 micrometers or less, in some embodiments from about 1 to about 500 micrometers, and in some embodiments, from about 10 to about 200 micrometers.

Figure 3:
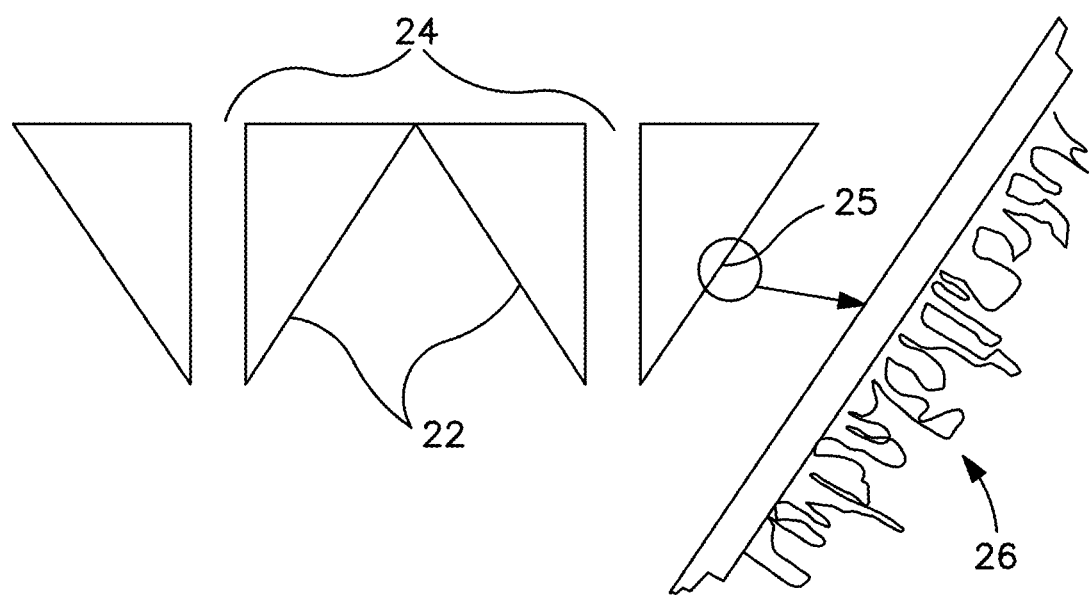

A microneedle surface may define a nanotopography thereon in a random or organized pattern. FIG. 3 schematically illustrates the ends of two representative microneedles 22. Microneedles 22 define a central bore 24 as may be used for delivery of an agent via the microneedles 22. The surface 25 of microneedles 22 define nanotopography 26. In this particular embodiment, the nanotopography 26 defines a random pattern on the surface 25 of the microneedle 22.

A microneedle may include a plurality of identical structures formed on a surface or may include different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

A microneedle surface defining a complex nanotopography may include structures of the same general shape (e.g., pillars) and the pillars may be formed to different scales of measurement (e.g., nano-scale pillars as well as micro-scale pillars). In another embodiment, a microneedle may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures can generally be greater than about 5 nanometers, for instance greater than about 10 nanometers, or greater than about 20 nanometers. For example, the nanostructures can define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

Figure 4:
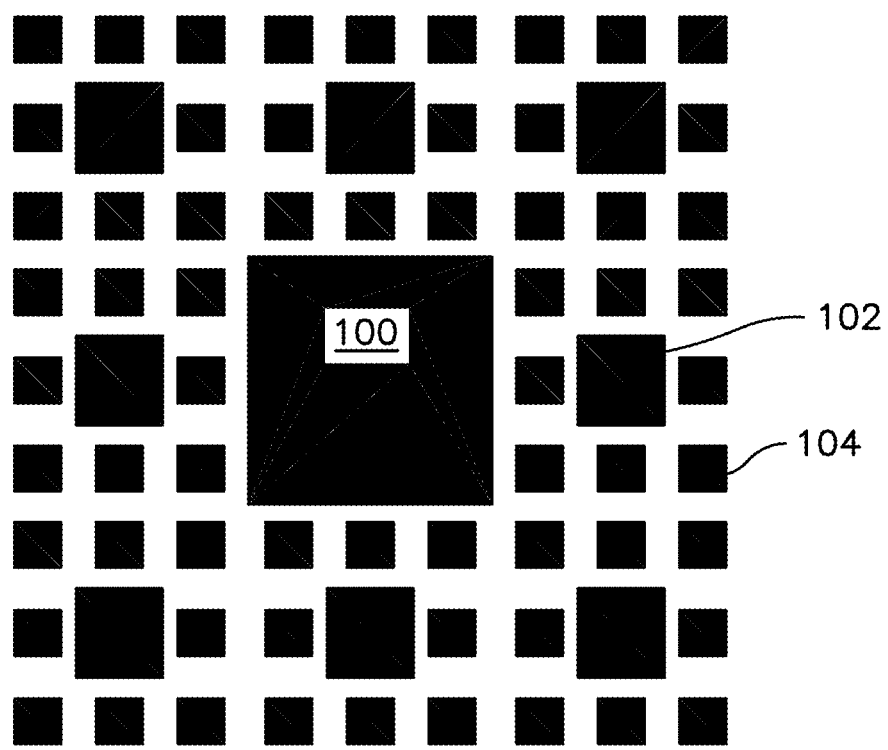

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes can include larger structures having a cross-sectional dimension formed on a larger scale, e.g., microstructures having a cross-sectional dimension greater than about 500 nanometers in combination with smaller nanostructures. In one embodiment, microstructures of a complex nanotopography can have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 4 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 4 have a cross-sectional dimension of about 400 nanometers, and pillars 104 have a cross-sectional dimension of about 200 nanometers.

A nanotopography can be formed of any number of different elements. For instance, a pattern of elements can include two different elements, three different elements, an example of which is illustrated in FIG. 4, four different elements, or more. The relative proportions of the recurrence of each different element can also vary. In one embodiment, the smallest elements of a pattern will be present in larger numbers than the larger elements. For instance in the pattern of FIG. 4, there are eight pillars 104 for each pillar 102, and there are eight pillars 102 for the central large pillar 100. As elements increase in size, there can generally be fewer recurrences of the element in the nanotopography. By way of example, a first element that is about 0.5 times, for instance between about 0.3 times and about 0.7 times in cross-sectional dimension as a second, larger element can be present in the topography about five times or more than the second element. A first element that is approximately 0.25 times, or between about 0.15 times and about 0.3 times in cross-sectional dimension as a second, larger element can be present in the topography about 10 times or more than the second element.

The spacing of individual elements can also vary. For instance, center-to-center spacing of individual structures can be between about 50 nanometers and about 1 micrometer, for instance between about 100 nanometers and about 500 nanometers. For example, center-to-center spacing between structures can be on a nano-sized scale. For instance, when considering the spacing of nano-sized structures, the center-to-center spacing of the structures can be less than about 500 nanometers. This is not a requirement of a topography, however, and individual structures can be farther apart. The center-to-center spacing of structures can vary depending upon the size of the structures. For example, the ratio of the average of the cross-sectional dimensions of two adjacent structures to the center-to-center spacing between those two structures can be between about 1:1 (e.g., touching) and about 1:4, between about 1:1.5 and about 1:3.5, or between about 1:2 and about 1:3. For instance, the center to center spacing can be approximately double the average of the cross-sectional dimensions of two adjacent structures. In one embodiment, two adjacent structures each having a cross-sectional dimension of about 200 nanometers can have a center-to-center spacing of about 400 nanometers. Thus, the ratio of the average of the diameters to the center-to-center spacing in this case is 1:2.

Structure spacing can be the same, i.e., equidistant, or can vary for structures in a pattern. For instance, the smallest structures of a pattern can be spaced apart by a first distance, and the spacing between these smallest structures and a larger structure of the pattern or between two larger structures of the pattern can be the same or different as this first distance.

For example, in the pattern of FIG. 4, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures can be equidistant from one another or any variation in distances. In one embodiment, different structures can be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, the aspect ratio of the nanostructures may fall within these ranges.

Figure 5:
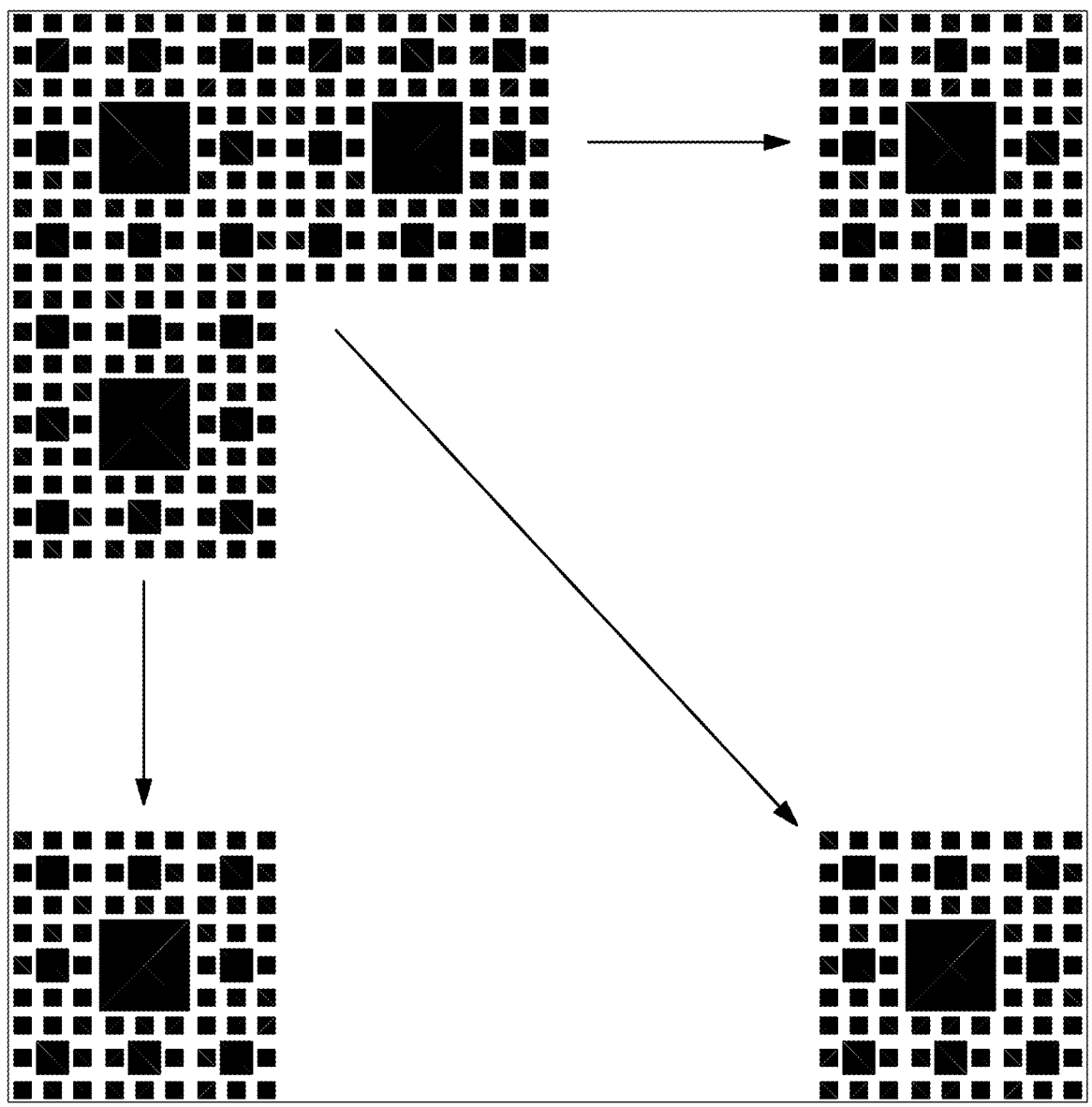

The device surface may include a single instance of a pattern, as shown in FIG. 4, or may include multiple iterations of the same or different patterns. For example, FIG. 5 illustrates a surface pattern including the pattern of FIG. 4 in multiple iterations over a surface.

The formation of nanotopography on a surface may increase the surface area without a corresponding increase in volume. Increase in the surface area to volume ratio is believed to improve the interaction of a surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins.

In general, the surface area to volume ratio of the device may be greater than about 10,000 cm$^{-1}$, greater than about 150,000 cm$^{-1}$, or greater than about 750,000 cm$^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference. The BET surface area can be less than about 5 m$^2$/g, in one embodiment, for instance between about 0.1 m$^2$/g and about 4.5 m$^2$/g, or between about 0.5 m$^2$/g and about 3.5 m$^2$/g. Values for surface area and volume may also be estimated from the geometry of molds used to form a surface, according to standard geometric calculations. For example, the volume can be estimated according to the calculated volume for each pattern element and the total number of pattern elements in a given area, e.g., over the surface of a single microneedle.

For a device that defines a complex pattern nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

Figure 6:
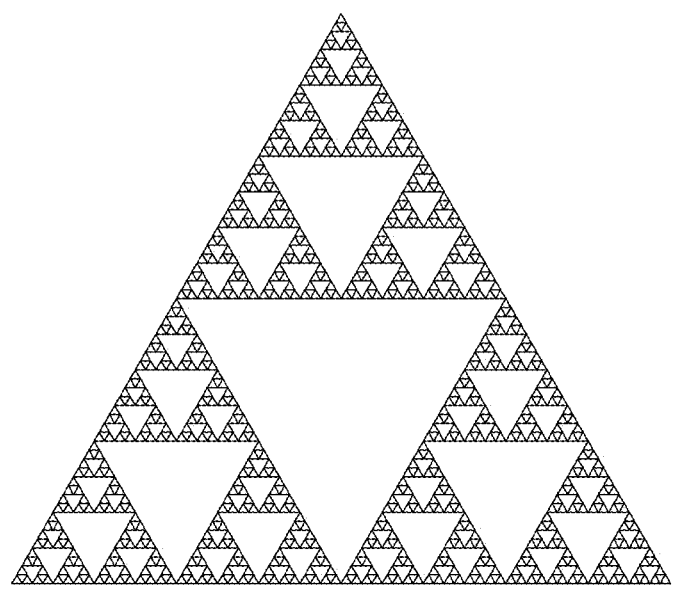

For example, when considering the two dimensional fractal known as the Sierpenski triangle illustrated in FIG. 6, in which the mid-points of the three sides of an equilateral triangle are connected and the resulting inner triangle is removed, the fractal dimension is calculated as follows:

$$D = \frac{\log N(e)}{\log(e)}$$
$$D = \frac{\log 3}{\log 2}$$
$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 4 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

Figure 7:
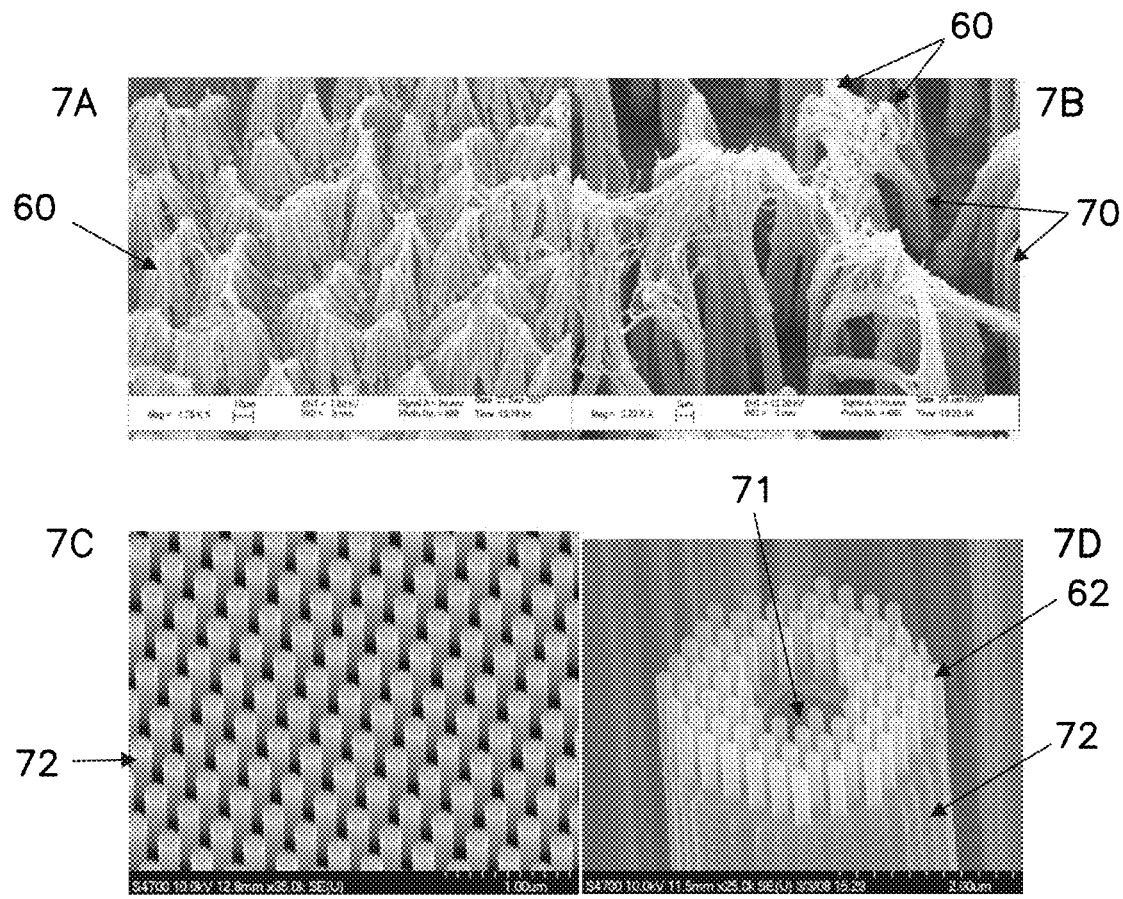

FIGS. 7A and 7B illustrate increasing magnification images of another example of a complex nanotopography. The nanotopography of FIGS. 7A and 7B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 7A and 7B). Structures formed on a surface that have an aspect ratio greater than about 1 may be flexible, as are the structures illustrated in FIGS. 7A and 7B, or may be stiff.

FIGS. 7C and 7D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 7C and 7D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 8:
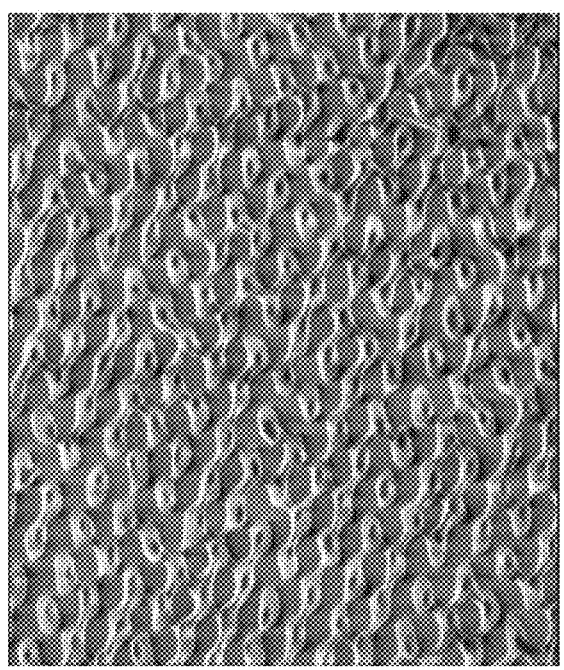

FIG. 8 illustrates another pattern including nano-sized structures as may be formed on the device surface. As may be seen, in this embodiment, individual pattern structures may be formed at the same general size, but with different orientations and shapes from one another.

In addition to or alternative to those methods mentioned above, a surface may be characterized by other methods including, without limitation, surface roughness, elastic modulus, and surface energy.

Methods for determining the surface roughness are generally known in the art. For instance, an atomic force microscope process in contact or non-contact mode may be utilized according to standard practice to determine the surface roughness of a material. Surface roughness that may be utilized to characterize a microneedle can include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The device may be characterized by the elastic modulus of the nanopatterned surface, for instance by the change in elastic modulus upon the addition of a nanotopography to a surface. In general, the addition of a plurality of structures forming nanotopography on a surface can decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the device including nanotopography thereon can exhibit a decrease in elastic modulus of between about 35% and about 99%, for instance between about 50% and about 99%, or between about 75% and about 80%. By way of example, the effective compression modulus of a nanopatterned surface can be less than about 50 MPa, or less than about 20 MPa. In one embodiment the effective compression modulus can be between about 0.2 MPa and about 50 MPa, between about 5 MPa and about 35 MPa, or between about 10 MPa and about 20 MPa. The effective shear modulus can be less than about 320 MPa, or less than about 220 MPa. For instance, the effective shear modulus can be between about 4 MPa and about 320 MPa, or between about 50 MPa and about 250 MPa, in one embodiment.

The device including nanotopography thereon may also exhibit an increase in surface energy as compared to a similar microneedle that does not have a surface defining a pattern of nanotopography thereon. For instance, a microneedle including a nanotopography formed thereon can exhibit an increase in surface energy as compared to a similar microneedle of the same materials and formed according to the same methods, but for the inclusion of a pattern of nanotopography on a surface. For instance, the water contact angle of a surface including a nanotopography thereon can be greater than about 80°, greater than about 90°, greater than about 100°, or greater than about 110°. For example, the water contact angle of a surface can be between about 80° and about 150°, between about 90° and about 130°, or between about 100° and about 120°, in one embodiment.

Figure 9A:
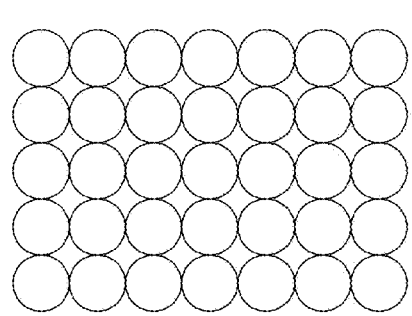
Figure 9B:
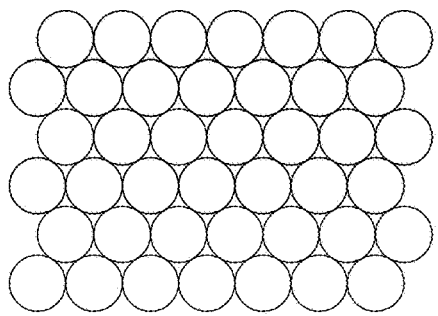
Figure 9C:
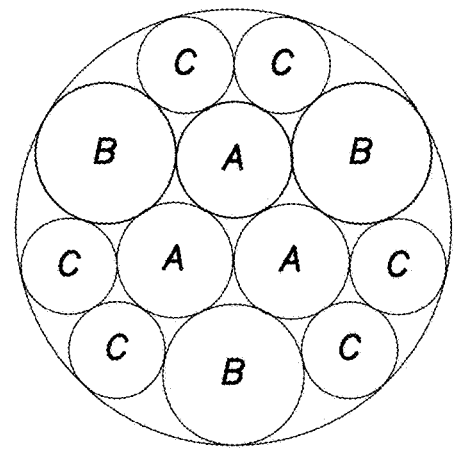

When forming nanostructures on the surface of the device, the packing density of the structures may be maximized. For instance, square packing (FIG. 9A), hexagonal packing (FIG. 9B), or some variation thereof may be utilized to pattern the elements on a substrate. When designing a pattern in which various sized elements of cross sectional areas A, B, and C are adjacent to one another on a substrate, circle packing as indicated in FIG. 9C may be utilized. Of course, variations in packing density and determination of associated alterations in characteristics of a surface are well within the abilities of one of skill in the art.

The device including a fabricated nanotopography on a surface of the device may be formed according to a single-step process. Alternatively, a multi-step process may be used, in which a pattern of nanostructures are fabricated on a pre-formed surface. For example, an array of microneedles may be first formed and then a random or non-random pattern of nanostructures may be fabricated on the surface of the formed microneedles. In either the single-step or two-step process, structures may be fabricated on a surface or on a mold surface according to any suitable nanotopography fabrication method including, without limitation, nanoimprinting, injection molding, lithography, embossing molding, and so forth.

In general, an array of microneedles may be formed according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

Lithography techniques, including photolithography, e-beam lithography, X-ray lithography, and so forth may be utilized for primary pattern definition and formation of a master die. Replication may then be carried out to form the device including an array of microneedles. Common replication methods include, without limitation, solvent-assisted micromolding and casting, embossing molding, injection molding, and so forth. Self-assembly technologies including phase-separated block copolymer, polymer demixing and colloidal lithography techniques may also be utilized in forming a nanotopography on a surface.

Combinations of methods may be used, as is known. For instance, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer demixing techniques. Structure diameter, shape, and pitch may be controlled via selection of appropriate materials and methods.

Figure 10A:
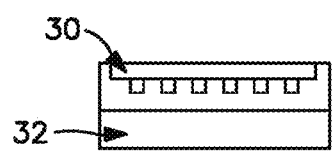
Figure 10B:
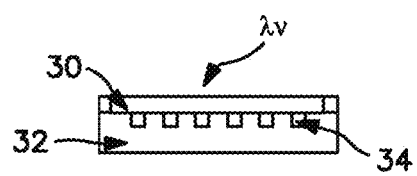
Figure 10C:
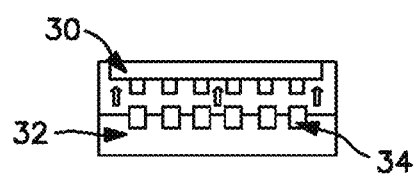

Other methods as may be utilized in forming a microneedle including a fabricated nanotopography on a surface include nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 10A-10C. During fabrication, a hybrid mold 30 imprints into a substrate 32 via applied pressure to form features (e.g., microneedles defining nanotopography) on a resist layer (FIG. 10A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 10B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below $T_g$ of the substrate and polymer (FIG. 10C).

To facilitate the release of the nanoimprinted substrate 32 including fabricated features 34 from the mold 30, as depicted in FIG. 10C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane ($F_{13}$-TCS).

Structures may also be formed according to chemical addition processes. For instance, film deposition, sputtering, chemical vapor deposition (CVD); epitaxy (vapor phase, liquid phase, and molecular beam), electroplating, and so forth can be utilized for building structures on a surface. Self-assembled monolayer processes as are known in the art can be utilized to form a pattern of structures on a surface.

The surface of a transdermal delivery device can be further functionalized for improved interaction with tissues or individual cells during use. For instance, one or more biomolecules such as polynucleotides, polypeptides, entire proteins, polysaccharides, and the like can be bound to a structured surface prior to use.

In some embodiments, a surface including structures formed thereon can already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a patterned device can include ECM proteins such as laminins, tropoelastin or elastin, Tropocollagen or collagen, fibronectin, and the like. Short polypeptide fragments can be bound to the surface of a patterned device such as an RGD sequence, which is part of the recognition sequence of integrin binding to many ECM proteins. Thus, functionalization of a microneedle surface with RGD can encourage interaction of the device with ECM proteins and further limit foreign body response to the device during use.

The transdermal delivery device may be in the form of a patch that may include various features. For example, the device may include a reservoir, e.g., a vessel, a porous matrix, etc., that may store and agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

Figure 11A:
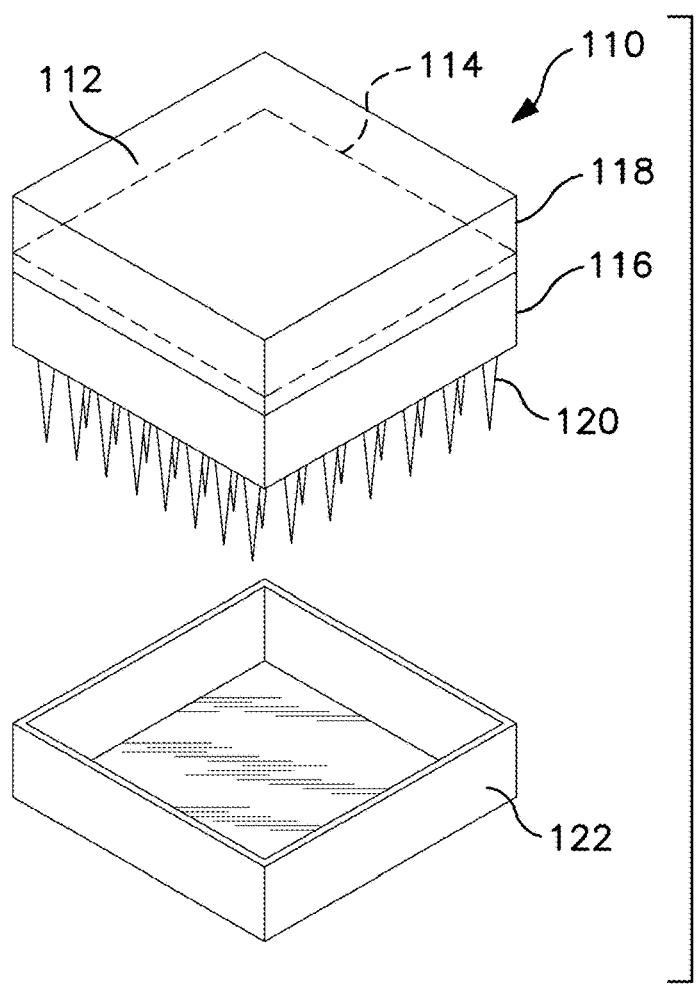
FIG. 11B illustrates the device of 11A during use.
Figure 11B:
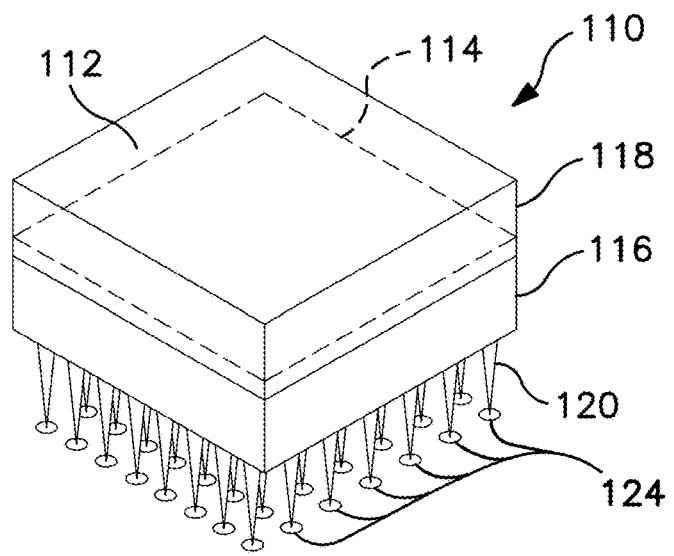

FIGS. 11A and 11B are perspective views of the device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 can be removed prior to use of the device to expose microneedles 120.

A formulation including one or more agents may be retained within the reservoir 112. Materials suitable for use as impermeable backing layer 114 can include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 14 and the microneedle array 16, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the substrate upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single or multiple agent-containing formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e., puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 12-17, one embodiment of a release member is shown that is configured to be detached from a transdermal patch to initiate the flow of a drug compound. More particularly, FIGS. 12-17 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Figure 12:
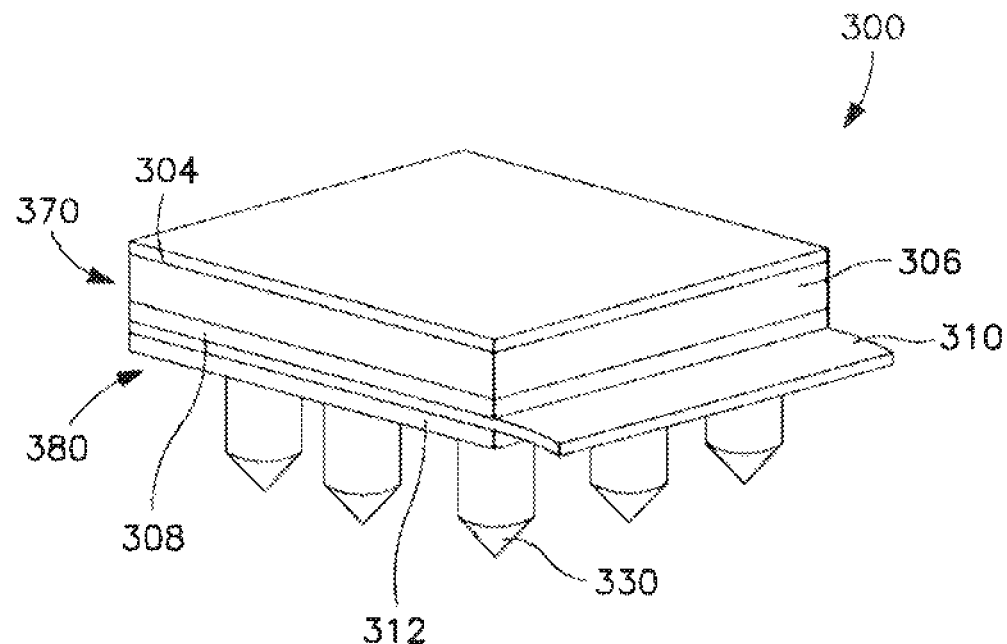
FIG. 12 is a perspective view of one embodiment of a transdermal patch prior to delivery of a drug compound.
Figure 13:
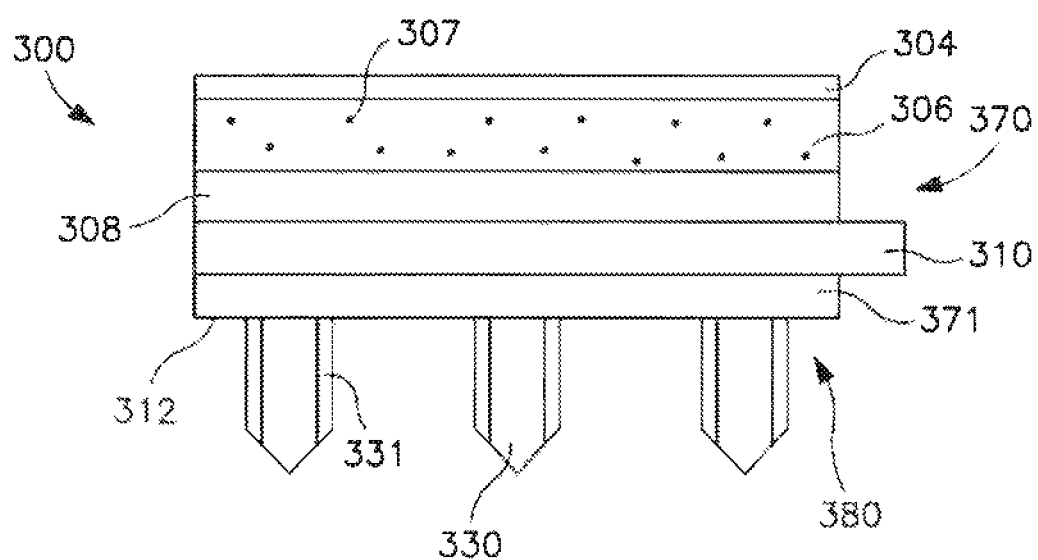
FIG. 13 is a front view of the patch of FIG. 12.

Referring to FIGS. 12-13, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 12-13) that extends at least partly beyond the perimeter of the patch 300 to facilitate the ability of a user to grab onto the member and pull it in the desired direction. In its "inactive" configuration as shown in FIGS. 12-13, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 14:
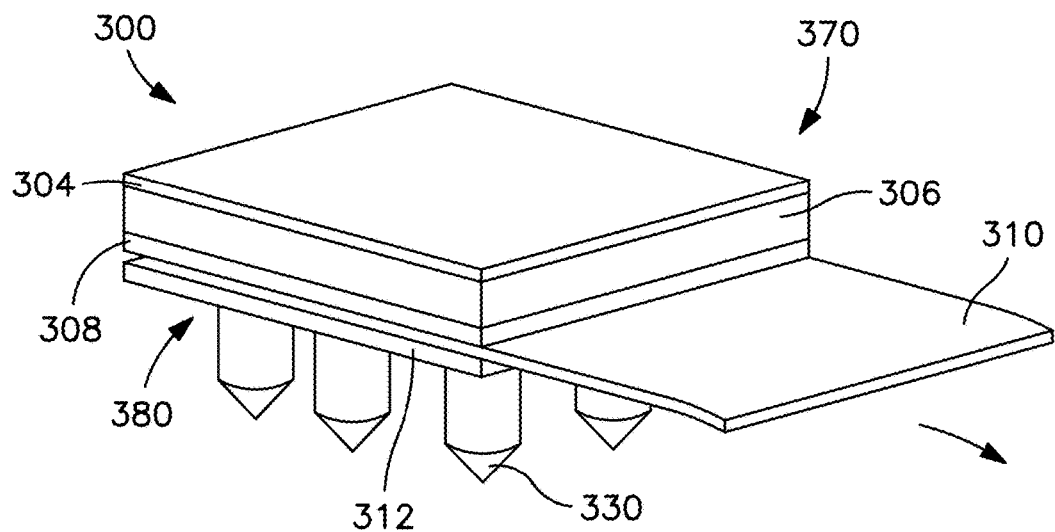
FIG. 14 is a perspective view of the patch of FIG. 12 in which the release member is partially withdrawn from the patch.
Figure 15:
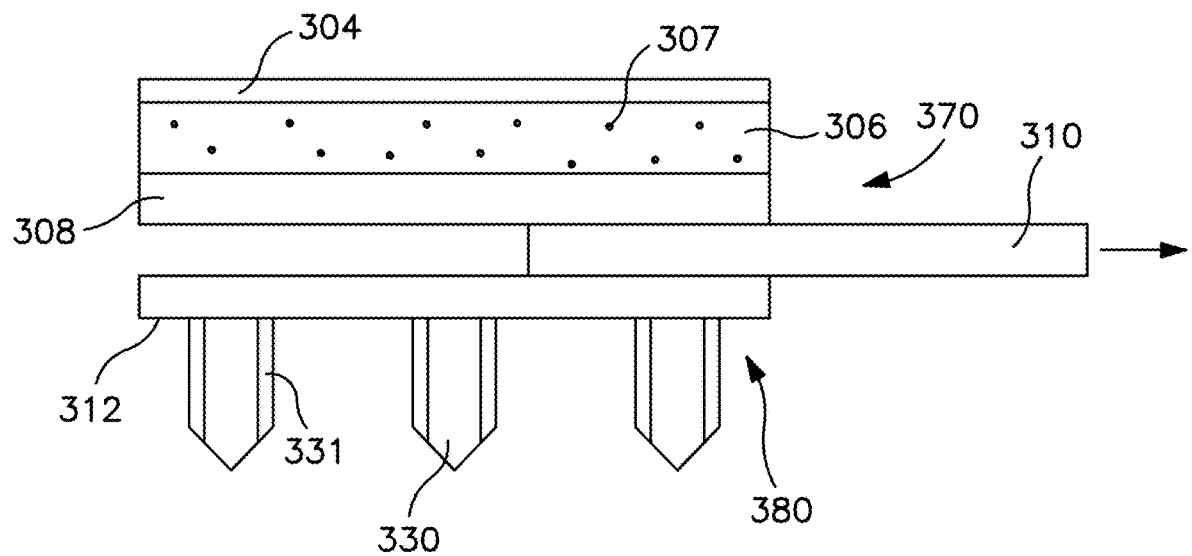
FIG. 15 is a front view of the patch of FIG. 14.
Figure 16:
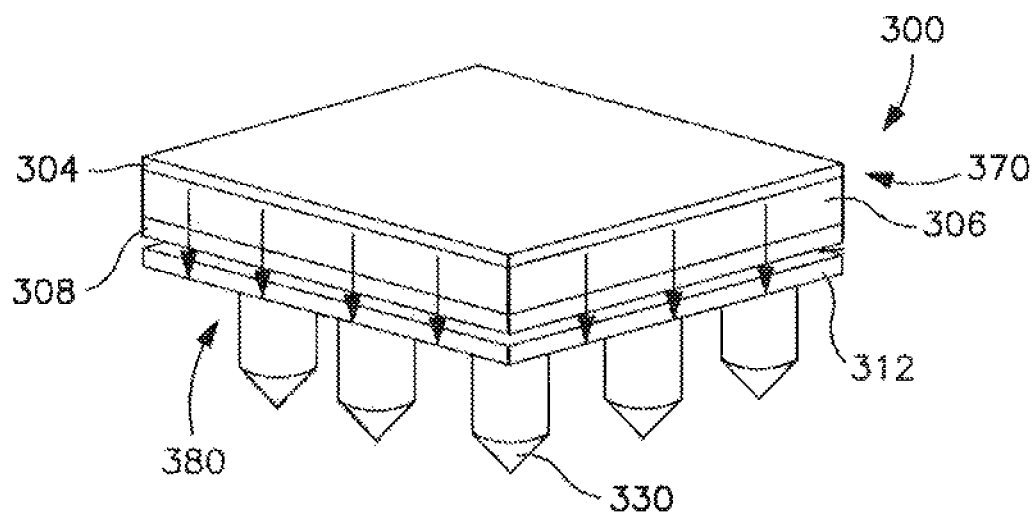
FIG. 16 is a perspective view of the transdermal patch of FIG. 12 after removal of the release member and during use.
Figure 17:
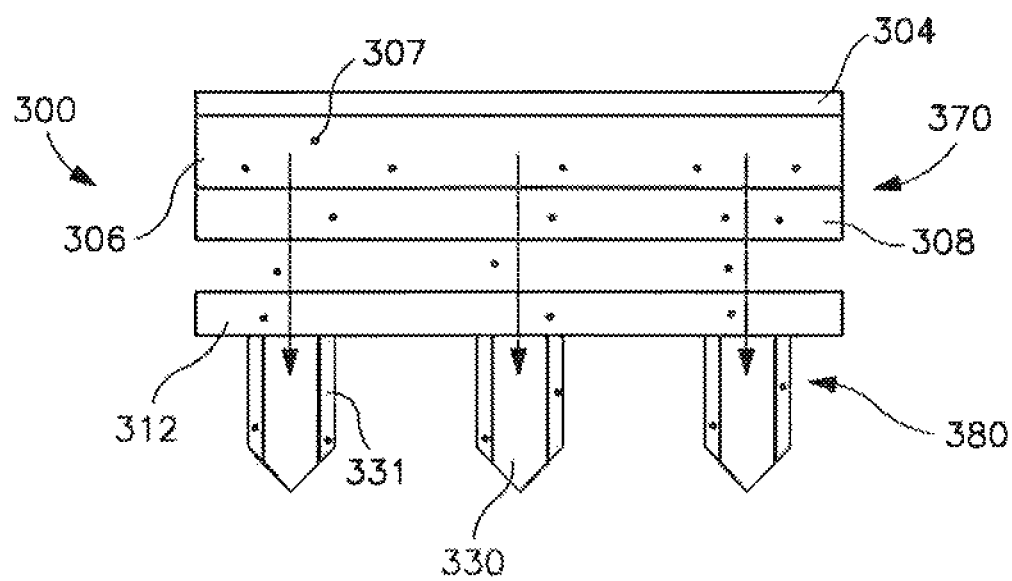
FIG. 17 is a front view of the patch of FIG. 16.

Referring to FIGS. 14-15, one embodiment for activating the patch 300 is shown in which the release member 310 is pulled in a longitudinal direction. The entire release member 310 may be removed as shown in FIGS. 16-17, or it may simply be partially detached as shown in FIGS. 14-15. In either case, however, the seal previously formed between the release member 310 and the aperture (not shown) of the support 312 is broken. In this manner, a drug compound 107 may begin to flow from the drug delivery assembly 170 and into the channels 131 of the microneedles 130 via the support 112. An exemplary illustration of how the drug compound 307 flows from the reservoir 306 and into the channels 331 is shown in FIGS. 16-17. Notably, the flow of the drug compound 307 is passively initiated and does not require any active displacement mechanisms (e.g., pumps).

In the embodiments shown in FIGS. 12-17, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 18:
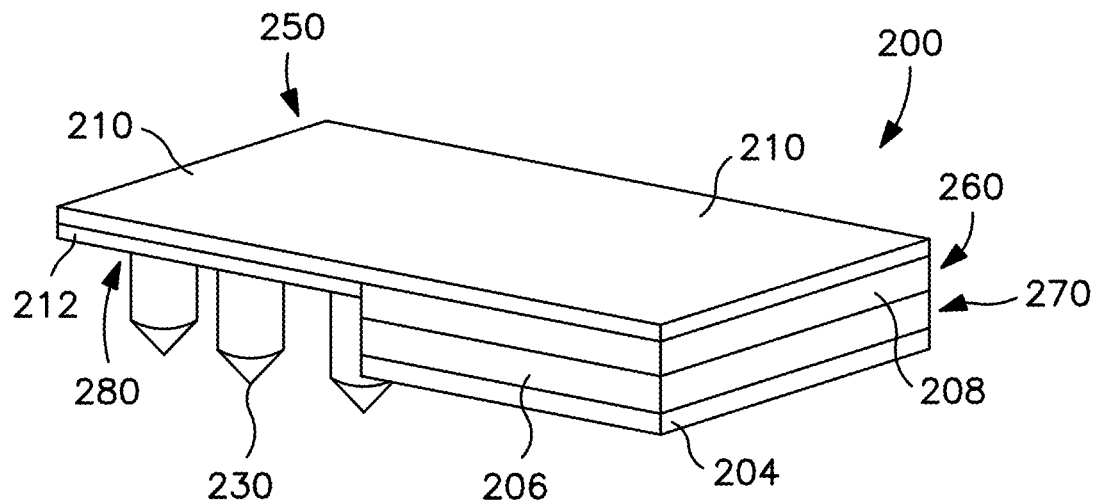
FIG. 18 is a perspective view of another embodiment of a transdermal patch prior to delivery of a drug compound.
Figure 19:
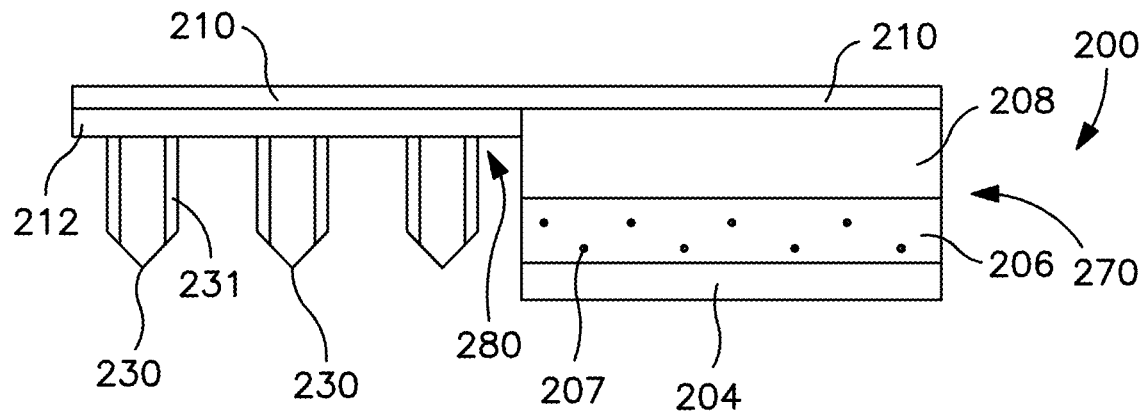
FIG. 19 is a front view of the patch of FIG. 18.

Referring to FIGS. 18-23, for example, one particular embodiment of a patch 200 is shown. FIGS. 18-19 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 20:
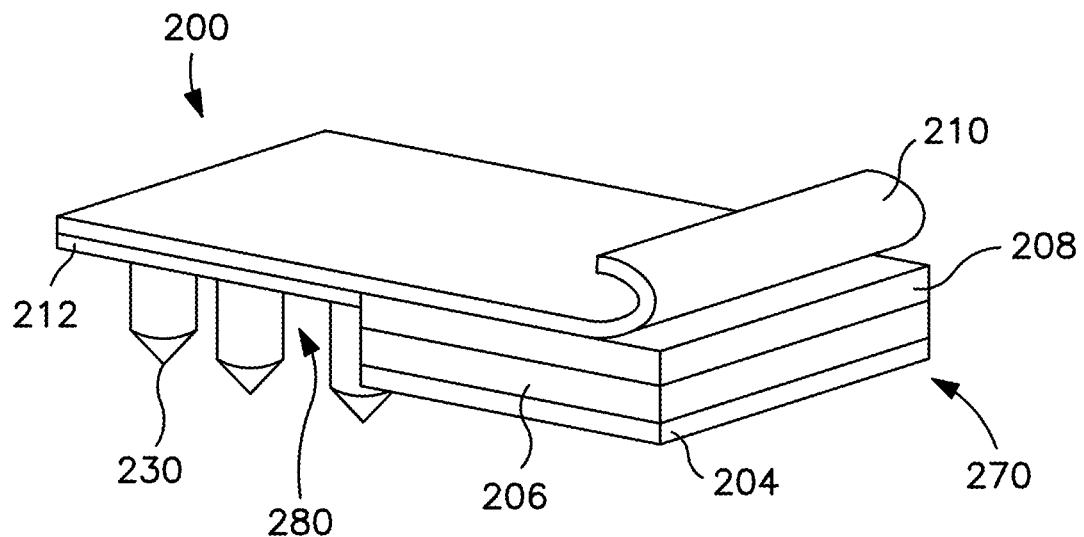
FIG. 20 is a perspective view of the patch of FIG. 18 in which the release member is partially peeled away from the patch.
Figure 21:
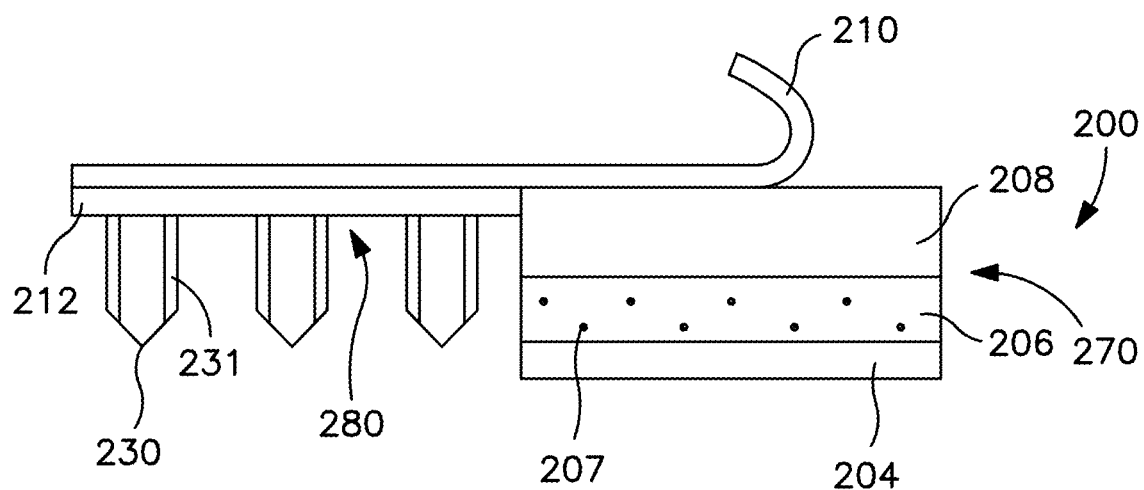
FIG. 21 is a front view of the patch of FIG. 20.
Figure 22:
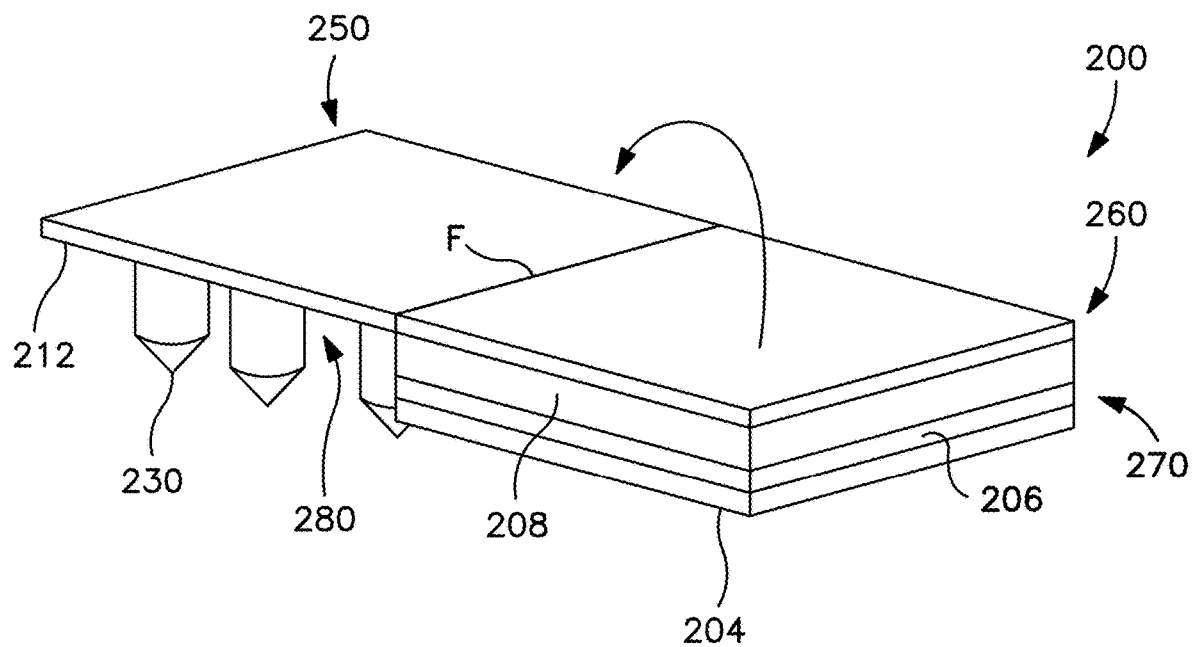
FIG. 22 is a perspective view of the patch of FIG. 18 in which the release member is completely peeled away from the patch.
Figure 23:
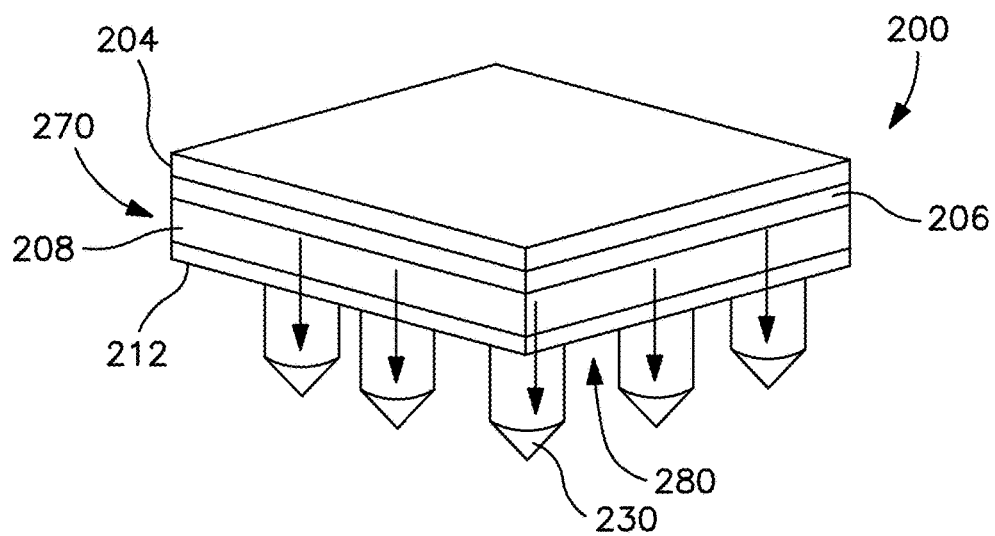
FIG. 23 is a perspective view of the transdermal patch of FIG. 18 after removal of the release member and during use.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 18-19, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 20-21, to break the seal previously formed between the release member 210 and the aperture (not shown) of the support 212. Thereafter, the second section 260 may be folded about a fold line "F" as shown by the directional arrow in FIG. 22 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 23).

The device may deliver an agent at a rate so as to be therapeutically useful. In accord with this goal, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may occur based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

The present disclosure may be further understood with reference to the Examples provided below.

Example 1

Several different molds were prepared using photolithography techniques similar to those employed in the design and manufacture of electrical circuits. Individual process steps are generally known in the art and have been described.

Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 $\mu C/cm^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm) He, 22 sccm $CF_4$, 20 sccm $C_4F_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm $Cl_2$ and 5 sccm Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 $W/cm^2$. A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Figure 24A:
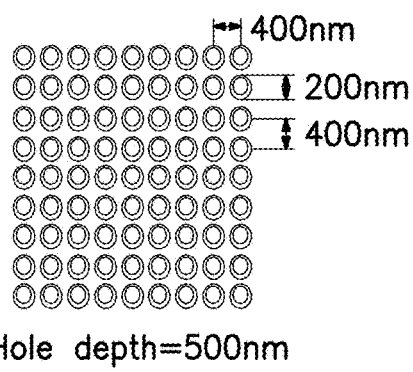
FIGS. 24A-24E illustrate several nanotopography patterns as described herein.
Figure 24A:
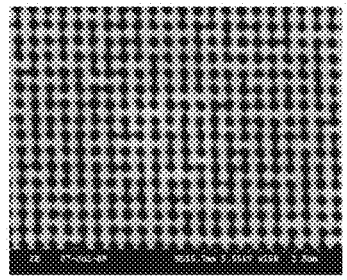
Figure 24B:
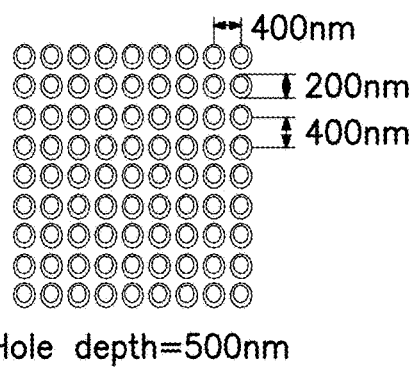
Figure 24B:
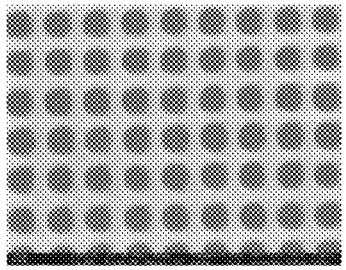
Figure 24C:
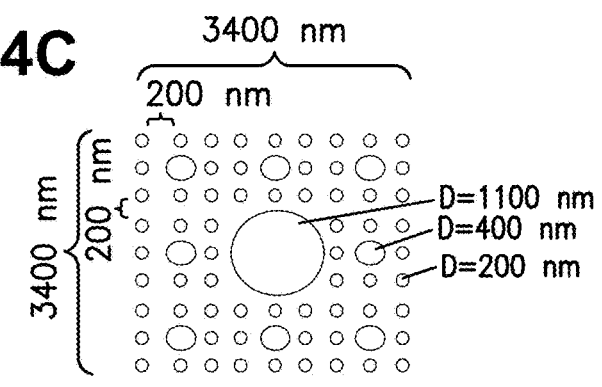
Figure 24C:
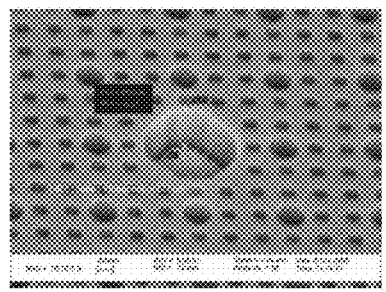
Figure 24D:
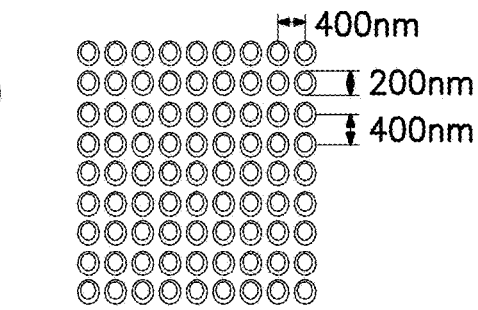
Figure 24D:
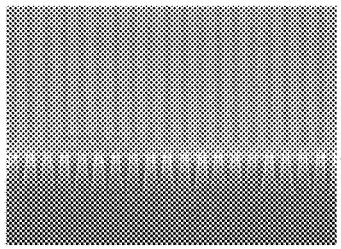
Figure 24E:
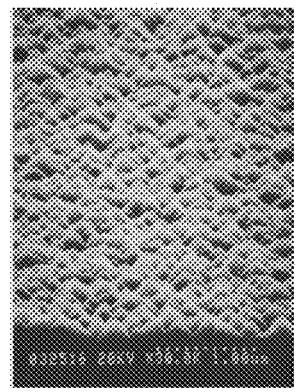

Several different nanotopography patterns were formed, schematic representations of which are illustrated in FIGS. 24A-24D. The nanotopography pattern illustrated in FIG. 24E was a surface of a flat substrate purchased from NTT Advanced Technology of Tokyo, Japan. The patterns were designated DN1 (FIG. 24A), DN2 (FIG. 24B), DN3 (FIG. 24C), DN4 (FIG. 24D) and NTTAT2 (FIG. 24E). SEM images of the molds are shown in FIGS. 24A, 24B, and 24C, and images of the films are shown in FIGS. 24D and 24E. FIG. 8 illustrates a nanopatterned film formed by use of the mold of FIG. 24A (DN1). In this particular film, the polymer features were drawn by temperature variation as previously discussed. The surface roughness of the pattern of FIG. 24E was found to be 34 nanometers.

The pattern illustrated in FIGS. 7C and 7D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature(C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

The permeability effects of films patterned as described above were determined on a monolayer of Caco-2 cells (human epithelial colorectal adenocarcinoma cells). The effects of the nanostructured surfaces on transcellular transport mechanisms were investigated by blocking Dynamin, a critical protein in endocytosis, with Dynasore. Dynamin is a large GTPase protein that self-assembles into a spiral shape, constricting around budding vesicles to free them from the plasma membrane and into the cytosol for transcellular transport. The small molecule, Dynasore, is able to rapidly block the activity of Dynamin by quickly inhibiting the GTPase module of Dynamin within about 2 minutes and has been used in numerous studies for probing the mechanisms of cellular internalization and endocytosis for transcellular transport. The transport study was a transepithelial electrical resistance (TEER) study that was carried out in the presence of Dynasore to biochemically block the activity of Dynamin and preclude both clathrin and caveolin mediated endocytosis.

Films formed as described in Example 1 and Example 2 were utilized including a polypropylene (PP) film formed with a pattern designated as DN2, and a flat, nonpatterned polypropylene film. As control, a monolayer of cells with no associated film was utilized.

The general protocol followed for each film was as follows:

Materials

Cell culture inserts 0.4 um pore size HDPET membrane (BD Falcon)
24 well plate (BD Falcon)
Caco-2 media
Nanostructured membranes as described above
Etanercept (Enbrel®)—a fusion protein therapeutic
Minimum Essential Medium no phenol red (Invitrogen)
TEER voltmeter
Warmed PBS
Black 96-well plate
Aluminum foil Protocol
1. Seed Caco-2 cells on collagen coated well inserts 2 weeks before permeability assay is to be performed. Collagen coated plates are made by making a 1:1 volume of 100% ethanol to collagen. Dry surfaces in sterile hood overnight until dry.
2. Make 0.1 mg/mL solution of Dynasore and FITC-conjugated etanercept in phenol red free Alpha MEM media. Wrap in aluminum foil to protect from light.
3. Check for confluence of Caco-2 cells by measuring the resistance. Resistance should be above ~600 Ohms for confluence.
4. Aspirate old media from cell culture inserts on apical and basolateral sides. Rinse with PBS to remove any residual phenol-red dye.
5. Add 0.5 mL of FITC-conjugated solution on apical side of each insert.
6. In another 24 well plate with cell culture inserts, add 0.5 mL of warmed PBS.
7. Transfer inserts to the plate with PBS. Blot the bottom of the insert on a Kim wipe to remove residual phenol red.
8. t=0—time point: sample 75 μL from the basolateral side of insert and transfer to a black-bottom 96-well plate. Replace the volume with 75 μL of warmed PBS. Record the resistance of each well using the "chopstick" electrodes.
9. Carefully add the film to the appropriately labeled well. Controls are the unimprinted film and the cells alone. Check under a microscope that the membranes make direct contact to the cells. You should be able to see a sharp circle, indicating contact with the cells.
10. t=0 time point: repeat step 7 and then place in the incubator for 1 hour
11. t=1 time point: repeat step 7 and then place in the incubator for 1 hour
12. t=2 time point: repeat step 7
13. Measure fluorescence signal using a spectrofluorometer plate reader. FITC (excitation=490 nanometers, emission=520 nanometers)

Figure 25:
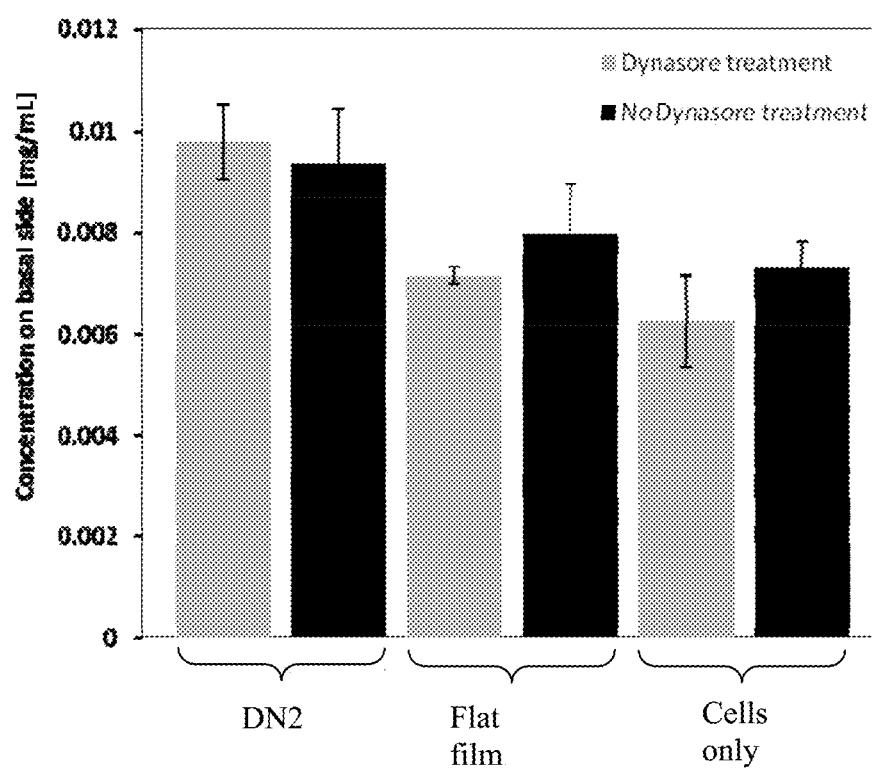
FIG. 25 illustrates the effect of blocking the transcellular delivery route on transport of a compound across an epithelial barrier according to disclosed methods.
Figure 26:
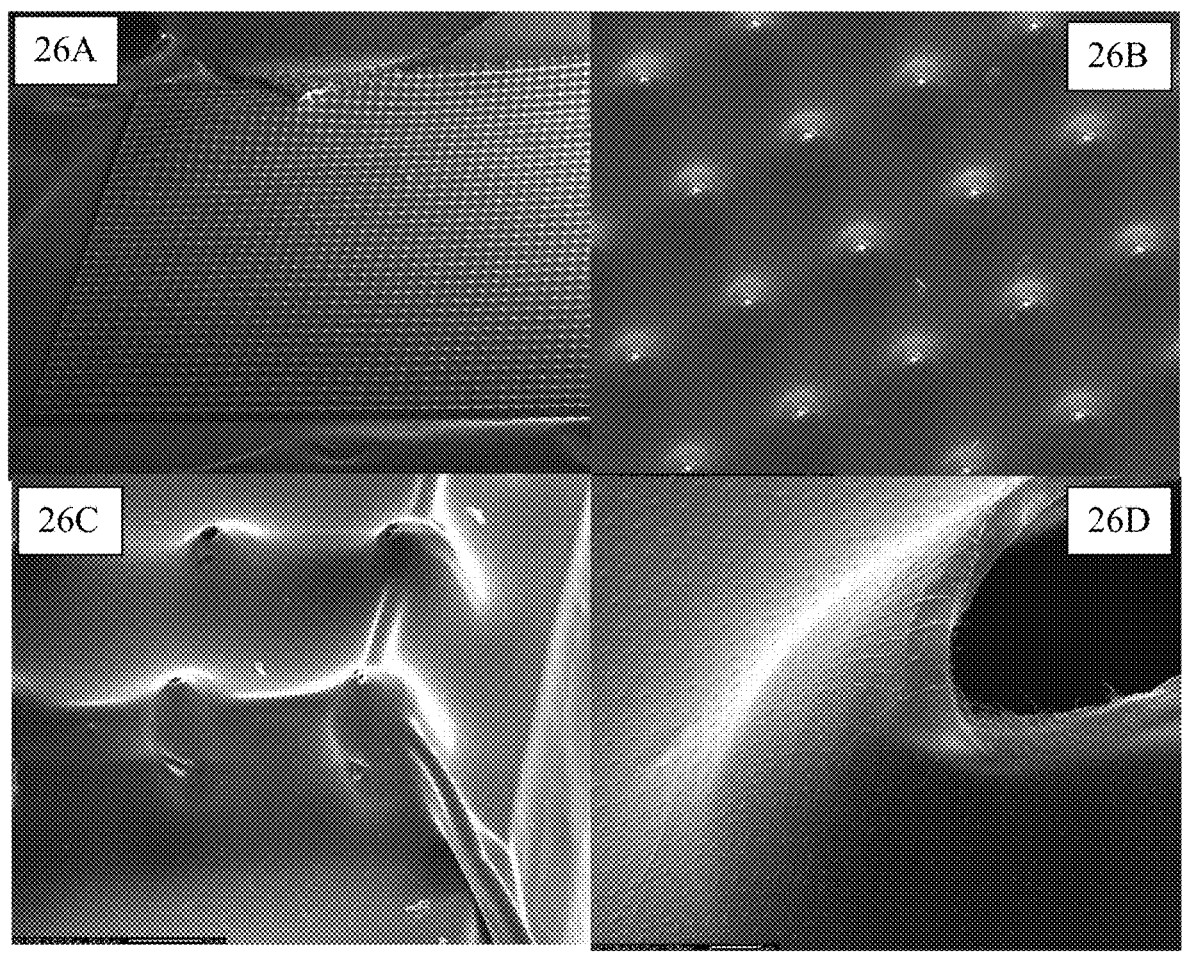
FIG. 26A illustrates a transdermal delivery device as described herein under magnification.
FIG. 26B illustrates a transdermal delivery device of FIG. 26A at greater magnification.
FIG. 26C illustrates a transdermal delivery device of FIG. 26B at even greater magnification.
FIG. 26D illustrates a transdermal delivery device of FIG. 26C at even greater magnification.

Results are shown in FIG. 25. As can be seen, blocking the transcellular delivery route did not significantly decrease etanercept transport across the layer. Therefore, the transcellular pathways related to Dynamin do not appear to be significantly affected by the nanostructures surface, and as such are believed to enhance paracellular transport through the tight junctions.

Example 3

An array of microneedles including a nanopatterned surface was formed. Initially, an array of microneedles as illustrated in FIG. 2 was formed on a silicon wafer via a photolithography process. Each needle included two oppositely placed side channels, aligned with one through-die hole in the base of the needle (not visible on FIG. 2).

Microneedles were formed according to a typical micromachining process on a silicon based wafer. The wafers were layered with resist and/or oxide layers followed by selective etching (oxide etching, DRIE etching, iso etching), resist stripping, oxide stripping, and lithography techniques (e.g., iso lithography, hole lithography, slit lithography) according to standard methods to form the array of microneedles. The microneedles were 300 microns tall and 100 microns in diameter.

Following formation of the microneedle array, a 5 μm polypropylene film including a DN2 or a polypropylene film including a DN3 pattern formed thereon as described above in Example 1 was laid over the microneedle array. The wafer/film structure was held on a heated vacuum box (3" $H_2O$ vacuum) at elevated temperature (130° C.) for a period of one hour to gently pull the film over the surface of the microneedles while maintaining the nanopatterned surface of the film.

FIGS. 26A-26D illustrate the DN2 patterned film over the top of the array of microneedles with increasing magnification forming a transdermal delivery patch.

The transdermal patches measured 25 mm by 25 mm with a density of 784 microneedles/cm². Control patches were also formed that had no pattern formed on the film subsequently applied to the array of microneedles. Transdermal and subcutaneous formulations of etanercept (Enbrel®) were prepared according to instructions from the drug supplier.

Test subjects (rabbits) were transdermally dosed with Enbrel® or were subcutaneously (SubQ) dosed with Enbrel®. Transdermal and subcutaneous formulations of etanercept (Enbrel®) were prepared according to instructions from the drug supplier. The subcutaneous dose formulation (for the positive control) was prepared to facilitate a 2.5 mg/animal and the transdermal dose formulation was 1.875 mg/animal. Two subjects were utilized for each device type.

Figure 27:
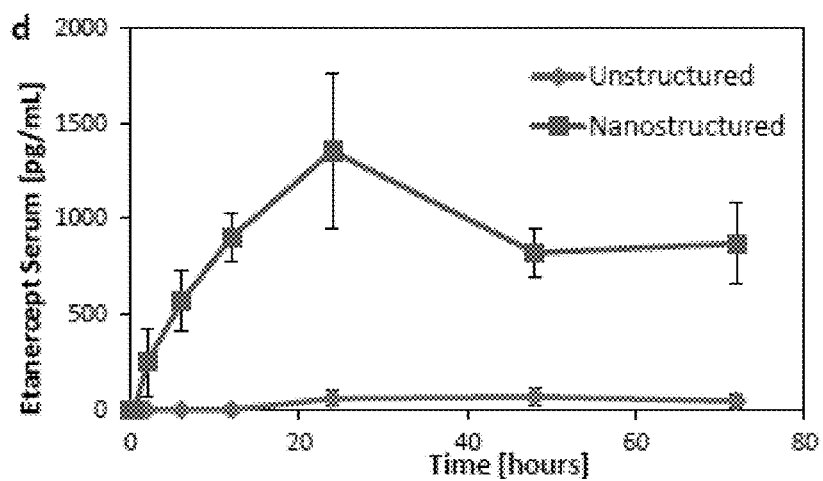
FIG. 27 is graphically illustrates the PK profile of a protein therapeutic delivered with a device as described herein.

Samples of whole blood were collected at the time points indicated in FIG. 27. Approximately 100 to 200 μl blood was taken via-mandibular bleeding and then centrifuged at approximately 1300 rpm for 10 minutes in a refrigerated centrifuge (set at 4° C.). The resulting serum was aspirated and transferred within 30 minutes of blood collection/centrifugation to appropriately labeled tubes. The tubes were frozen and stored in the dark at ≤−70° C. until they were analyzed for levels of Enbrel® using Human sTNF-receptor ELISA kit (R&D Systems cat # DRT200). The space time between two blood samplings on the same subject was 24 hours, to prevent unnecessary stress placed on the subject.

The pharmacokinetic curve for the control patch and the DN3 patch are shown in FIG. 27. As can be seen, the blood serum level of the etanercept rose rapidly with the DN3 transdermal patch within the first 24 hours of attachment. Following, the blood serum level gradually declined within 56 hours of attachment and then leveled off. The control patch provided very low levels of etanercept with a gradual rise to a peak level at approximately 48 hours.

The results indicate that the nanostructured microneedles significantly increased the absorption of etanercept as compared to the flat, unstructured device. There is a 95% increase in the maximum concentration measure and the time to reach the maximum concentration is decreased by almost 24 hours. In addition, the bioavailability of the materials delivered by use of the nanostructured D3 device was found to be about 35 times greater than the control patch.

After 72 hours, several different organs and tissue types in each subject were examined for etanercept concentration. Specifically, organ representative samples of approximately 100 mg each were placed in labeled 50 mL conical storage tubes and stored in the dark at approximately −70° C. for preservation testing.

For analysis of Enbrel levels in tissues at the analytical laboratory, tissues were tested by use of a Quantikine® Human sTNF RII/TNFRSF1B Immunoassay (catalog no. DRT200, SRT200, PDRT200) available from R&D Systems, Inc. of Minneapolis, Minn., USA. The immunoassay is a solid phase ELISA assay for determination of sTNF RII. The protein was measured against the standard provided with the kit, and etanercept was measured against a standard curve, with concentrations based on the dosage details.

Results are shown in Table 3, below. All concentrations are provided as ng/g tissue. The ELISA detection mechanism could be utilized for concentrations down to about 0.6 pg/m L. Results of <MIN signify a concentration too low to be determined by the ELISA assay. Results of N/A indicate an error in the ELISA assay, with no reportable results obtained.

TABLE 3

| Organ | Subcutaneous | Control Film | DN3 pattern |
| --- | --- | --- | --- |
| lateral aortic lymph node | 41.47 | 91.44 | <MIN |
| liver | 62.41 | 1.31 | <MIN |
| pancreas | 16.69 | <MIN | <MIN |
| skin | 172.09 | 206.44 | N/A |
| spleen | 9.25 | 4.97 | <MIN |
| lung | 23.76 | <MIN | <MIN |
| kidney | 10.14 | 10.66 | 11.3 |
| bone marrow | 13.72 | 1.63 | 2.09 |

Both the PK curves of FIG. 27 and the organ distribution information of Table 3 suggest that the nanostructured microneedles increase drug uptake by the bloodstream and minimize absorption by the lymphatic system.

Example 4

Figure 28:
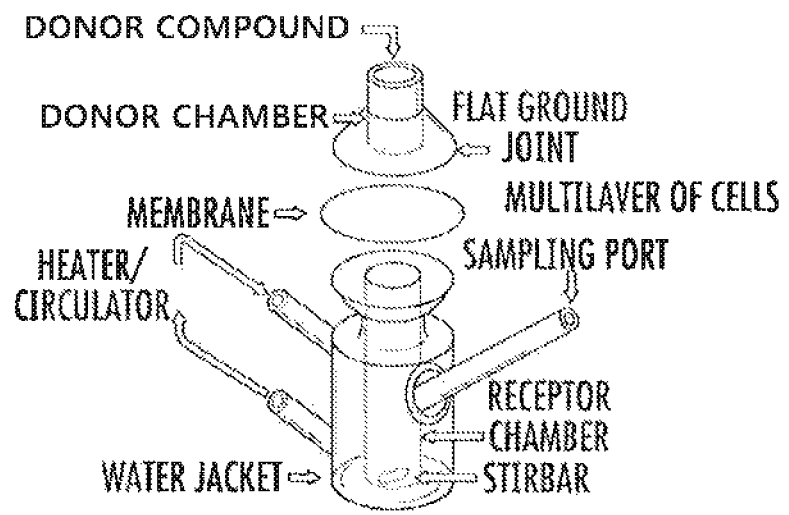
FIG. 28 is a schematic diagram of a sample chamber utilized in the Example section.

A device as illustrated in FIG. 28 was assembled including a film (i.e., a membrane) defining a pattern of nanostructures on a surface thereof. The film was formed as described above in Example 1 and was a polypropylene film including a DN2 pattern on the surface thereof. An EpiDerm™ tissue, a three dimensional construct organized into basal, spinous, and granular layers along a multi-layered stratum corneum available from MatTek Corporation, was located on the surface of the film as described above with regard to the monocellular layer.

A 1 mg/mL composition including the high molecular weight drug etanercept (Enbrel®) was prepared. Etanercept is a fusion protein having a molecular weight of 150 kDa. Phosphate buffered saline was located in the receptor chamber. The system was incubated at 37° C. and samples were withdrawn every five hours.

The composition was loaded in to the donor chamber on one side of an EpiDerm™ tissue either on the DN2 nanostructure film or on a polypropylene film with no nanopattern formed thereon (PPUI), and samples were withdrawn from the receptor chamber on the other side of the cell layer, as illustrated in FIG. 28. As can be see with reference to FIG. 29, following one hour, very little etanercept had passed into the receptor chamber for the control, while there was approximately a 1.7 fold increase in the amount of etanercept in the receiver chamber for the sample on the DN2 patterned film. After two hours, there was an approximately 2-fold increase for the system including the DN2 patterned film.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for delivering a bioactive agent to a subject comprising:
    penetrating the stratum corneum of the subject with a microneedle that contains a channel in fluid communication with the bioactive agent, the microneedle including a plurality of nanostructures and microstructures formed on an external surface thereof in a pattern, wherein at least a portion of the microstructures have a cross-sectional dimension of greater than about 500 nanometers and less than about 10 micrometers and a height of from about 20 nanometers to about 1 micrometer, the cross-sectional dimension of the microstructures being greater than the height of the microstructures, and wherein at least a portion of the nanostructures have a cross-sectional dimension of greater than about 5 nanometers and less than about 500 nanometers;
    transporting the bioactive agent through the channel of the microneedle, wherein the channel is surrounded by the external surface of the microneedle; and
    delivering the bioactive agent to the subject with a comparative bioavailability as compared to subcutaneous delivery of greater than about 20%.

2. The method according to claim 1, wherein the bioactive agent is delivered to the subject such that the concentration of the bioactive agent in lymph node tissue of the subject is less than about 50 nanograms per gram of the lymph node tissue about 72 hours after penetrating the stratum corneum of the subject.

3. The method according to claim 1, wherein the concentration of the bioactive agent in the lymph node is less than about 10 nanograms per gram of the lymph node about 72 hours after the application of the transdermal delivery device to the skin surface.

4. The method according to claim 1, wherein the concentration of the bioactive agent in the lymph node is less than about 1 nanogram per gram of the lymph node about 72 hours after the application of the transdermal delivery device to the skin surface.

5. The method according to claim 1, the subject having a spleen, wherein the concentration of the bioactive agent in a sample of the spleen tissue is less than about 5 nanograms per gram of the sample of the spleen tissue about 72 hours after the application of the transdermal delivery device to the skin surface.

6. The method according to claim 5, wherein the concentration of the bioactive agent in a sample of the spleen tissue is less than about 1 nanogram per gram of the sample of the spleen tissue about 72 hours after the application of the transdermal delivery device to the skin surface.

7. The method according to claim 1, the subject having a liver, wherein the concentration of the bioactive agent in a sample of the liver tissue is less than about 50 nanograms per gram of the sample of liver tissue about 72 hours after the application of the transdermal delivery device to the skin surface.

8. The method according to claim 7, wherein the concentration of the bioactive agent in a sample of the liver tissue is less than about 1 nanogram per gram of the sample of the liver tissue about 72 hours after the application of the transdermal delivery device to the skin surface.

9. The method according to claim 1, further comprising second nanostructures having a cross-sectional dimension less than the cross-sectional dimension of the microstructures and greater than the cross-sectional dimension of the plurality of nanostructures.

10. The method according to claim 1, wherein the stratum corneum is a layer of the subject's skin, the skin including tight junctions between cells of the skin, the nanostructures rearranging tight junctions between the cells, thereby increasing porosity of the skin.

11. The method according to claim 10, wherein the rearrangement of the tight junctions leads to an increase in the porosity of a second tissue type that is not in contact with the microneedle.

12. The method according to claim 11, wherein the second tissue type is vascular tissue.

13. The method according to claim 1, wherein the pattern has a fractal dimension of greater than about 1.

14. The method according to claim 1, wherein the pattern has a fractal dimension of from about 1.5 to about 2.5.

15. The method according to claim 1, wherein the microneedle surface containing the plurality of nanostructures has an average surface roughness between about 10 nanometers and about 200 nanometers.

16. The method according to claim 1, wherein the microneedle surface containing the plurality of nanostructures has an effective shear modulus between about 4 MPa and about 320 MPa.

17. The method according to claim 1, wherein the bioactive agent has a molecular weight of greater than about 100 kDa.

18. The method according to claim 17, wherein the bioactive agent is a protein therapeutic.

19. The method according to claim 1, wherein the channel has a cross-sectional dimension of from about 1 to about 100 micrometers.

20. The method according to claim 19, wherein the channel has a length of from about 10 to about 800 micrometers.

21. The method according to claim 1, wherein at least a portion of the nanostructures have a cross-sectional dimension of from about 20 to about 400 nanometers and at least a portion of the microstructures have a cross-sectional dimension of from about 600 nanometers to about 1.5 micrometers.

22. The method according to claim 1, wherein the nanostructures have approximately the same cross-sectional dimension.

23. The method according to claim 1, wherein the ratio of the cross sectional dimension of two adjacent nanostructures to the center-to-center spacing between those two structures is between about 1:1 and about 1:4.

24. The method according to claim 1, wherein at least a portion of the nanostructures have an equidistant spacing.

25. The method according to claim 1, where at least a portion of the nanostructures have a height of from about 20 nanometers to about 1 micrometer.

26. The method according to claim 1, wherein at least a portion of the nanostructures have an aspect ratio of from about 0.2 to about 5.

27. The method according to claim 1, wherein at least a portion of the nanostructures have an aspect ratio of from about 0.5 to about 3.5.

28. The method according to claim 1, wherein at least a portion of the microstructures have an aspect ratio of from about 0.15 to 1.

29. The method according to claim 1, wherein at least a portion of the nanostructures have a center-to-center spacing of from about 50 nanometers to about 1 micrometer.

30. The method according to claim 1, wherein the nanostructures are in the form of pillars, the pillars having a base adjacent to the external surface of the microneedle and extending in a generally longitudinal direction to a tip.

31. The method according to claim 1, wherein at least a portion of the nanostructures have a height greater than a cross-sectional dimension.

* * * * *